(12) United States Patent
Diner et al.

(10) Patent No.: US 6,350,573 B1
(45) Date of Patent: Feb. 26, 2002

(54) METHODS FOR IDENTIFYING HERBICIDAL AGENTS THAT INHIBIT D1 PROTEASE

(75) Inventors: Bruce Aaron Diner, Chadds Ford, PA (US); Douglas Brian Jordan, Wilmington; Xiao-Song Tang, Hockessin, both of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/304,711

(22) Filed: May 4, 1999

Related U.S. Application Data

(63) Continuation-in-part of application No. 09/173,281, filed on Oct. 15, 1998, which is a continuation of application No. 08/759,581, filed on Aug. 4, 1998, now abandoned.

(51) Int. Cl.$^7$ ................................................. C12Q 1/00
(52) U.S. Cl. ............................... 435/4; 435/4; 435/219; 435/252.31; 435/254.11; 435/254.2; 435/348; 536/23.1
(58) Field of Search ........................ 435/219, 4, 252.3, 435/252.31, 254.11, 254.2, 348; 536/23.1

(56) References Cited

PUBLICATIONS

Satoh, K. Isolated and Properties of the Photosystem II Reaction Center, *The Photosynthetic Reaction Center*, vol. I, pp:289–318 (1993).
Siebert, M., Biochemical, Biophysical, and Structural Characterization of the Isolated Photosystem II Reaction Center Complex, Deisenhofer, J. and Norris, J.R., eds. *The Photosynthetic Reaction Center*, Academic Press, New York, vol. I, pp:319–356 (1993).
Grebanier, A.E. et al., Membrane Proteins Synthesized but not processed by Isolated Maize Chloroplasts, *J. Cell Biol.*, 78, pp: 734–746 (1978).
Reisfeld et al., Processing of a Chloroplast–Translated Membrane Protein in vivo, Analysis of the Rapidly Synthesized 32000–dalton Shield Protein and Its Precursor in *Spirodela oligorrhiza*, Dept of Plant Genetics, The Weismann Institute of Science, Rehovot, Eur. J. Biochem. 124, pp. 125–129 (1982).
Minami, J.B. and Watanabe, Detection of a Precursor Polypeptide of the Rapidly–Synthesized 32,000–Dalton Thylakoid Protein in Spinach Chloroplasts, A. *Plant. Cell Physiol.* 26, pp: 839–846 (1985).
Marder, J.B. et al., Molecular Architecture of the Rapidly Metabolized 32–kilodalton Protein of Photosystem II, *J. Biol. Chem.* 259, 3900–3908 (1984).
Diner, B.A. et al., COOH–terminal Processing of polypeptide D1 of the photosystem II reaction center of *scenedesmus obiquus* is necessary for the assembly of the oxygen–evolving complex., 263, pp. 8972–8980 (1988).

Nixon, P.J., Trost, J.T. and Diner, B.A., Role of the Carboxy Terminus of Polypeptide D1 in the Assembly of a Functional Water–Oxidizing Manganese Cluster in Photosytem II of the Cyanobacterium Synechocystis sp. PCC 6803: Assembly Requires a Free Carboxyl Group at C–Terminal Position 344; *Biochemistry* 31: pp.10859–10870 (1992).
Takahashi et al., COOH–terminal residues of D1 and the 44 kDa Cpa–2 at spinach photosystem II core complex, *FEBS Lett.* 06485 vol. 240, No. 1, 2, pp: 6–8 (1988).
Takahashi et al., Chromatographic Purification and Determination of the Carboxy–Terminal Sequences of Photosystem II Reaction Center Proteins, D1 and D2, Plant Cell Physiol.. 31, 273–280 (1990).
Taylor, M.A. et al., Characterization of the D1 protein in a photosystem II mutant (LF–1) of *scenedesmus obliquus* blocked on the oxidizing side. Evident supporting non–processing of D1 as the cause of the lesion, FEBS Letters 235: pp. 109–116 (1988).
Shestakov, S.V. et al., Molecular Cloning and Characterization of the ctpA Gene Encoding a Carboxy–terminal Processing Protease, Journal of Biological Chemistry 269: pp. 1–6 (1994).
Anbudurai, P.R. et al., The ctpA gene encodes the C–terminal processing protease for the D1 protein of the photosystem II reaction center complex, Proceedings of the National Science, USA,, 91, pp. 8082–8086 (1994).
Fujita, S. et al. Identification of the Carboxyl–Terminal Processing Protease for the D1 Precursor Protein of the Photosystem II Reaction Center of Spinach, Plant Cell Physiol., 36(7), 1169–1177 (1995).
Inagaki, N. et al., Carboxyl–terminal processing protease for the D1 precursor protein: cloning and sequening of the spnach cDNA, Plant Molecular Biology 30 pp: 39–50 (1996).
Taguchi et al., Recognition of the Structure around the Site of Cleavage by the Carboxyl–terminal Processing Protease for D1 Precursor Protein of the Photosystem II Reaction Center, *J. Biol. Chem.*, 270(18), pp:10711–16 (1995).
Packer et al., Curr. Res. Photosynth., Proc. Int. Conf. Photosynth., 8th (1990), Meeting Date 1989, vol. III.13, pp: 759–762. Editor(s): Baltscheffsky, Margareta. Publisher: Kluwer, Dordrecht, Netherlands.
Magnin et al., Preliminary Steps in the Purification of the Photosystem II D1 Protein Processing Protease from Maize, *Res. Photosynth.*, Proc. Int. Congr. Photosyn., 9th (1992), vol. II, pp: 211–214: Editor(s): Murata, N. Publisher: Kluwer, Dordrecht, Netherlands (1992).

(List continued on next page.)

*Primary Examiner*—Karen Cochrane Carlson
*Assistant Examiner*—Hope A. Robinson

(57) ABSTRACT

D1 protease has been isolated from the alga (*Scenedesmjus obliquus*), wheat, and Synechocystis PCC 6803 and the genes encoding these enzymes have been cloned and sequenced. Native or recombinantly produced enzyme has been used to develop assays to detect herbicidal compositions capable of inhibiting the D1 protease enzyme.

7 Claims, 6 Drawing Sheets

OTHER PUBLICATIONS

Silber, K.R. et al., Tsp: A tail–specific protease that selectively degrades proteins with nonpolar C termini. Proceedings of the National Science, USA, 89: pp.295–299 (1992).

Hara et al., Cloning, Mapping, and Characterization of the *Escherichia coli* prc Gene, Which Is Involved in C–Terminal Processing of Penicillin–Binding Protein 3, J. Bacteriol. vol. 173, No. 15, pp.4799–4813 (1991).

Hunt, A. P., Hussey and J. Bowyer, The Production of Trucated Substrates for the D1 processing protease of Photosystem II, Research in Photosynthesis, N. Murata, Editor; Kluwer Academic Publishers, pp. 207–210 (1992).

Keiler, K.C. and Sauer, R.T., Identification of Active Site Residues of the Tsp Protease, Journal of Biological Chemistry, vol. 270, No. 48: pp: 28864–28868 (1996).

Oelmuller, R. et al., Molecular Studies of ctpA, the Carboxyl–terminal Processing Protease for the D1 Protein of the Photosystem II Reaction Center in Higher Plants, Journal of Biological Chemistry vol. 271, No. 36, pp: 21848–21852 (1996).

Pakrasi, H.B. et al., Molecular Analysis of ctpA, the Carboxyl–Terminal Processing Protease for the D1 protein of Photosystem II, in Higher Plants and Cyanobacteria, Photosynthesis: from Light to Biosphere, Kluwer Academic Publishers, pp: 719–724 (1995).

Boyer, J.R. et al., Carboxyl–terminal Processing of the D1 Protein and Photoactivation of Water–splitting in Photosystem II., Journal of Biological Chemistry, 267, pp: 5424–5433 (1992).

Fujita, S. et al., Cleavage of a synthetic COOH–terminal oligopeptide of D1 precursor protein by a purified processing enzyme., FEBS Letters, 225, pp: 1–4 (1989).

Inagaki, N., Fujita, S. and Satoh, K., Solubilization and partial purification of a thylakoidal enzyme of spinach involved in the processing of D1 protein, FEBS Letters, 246: pp: 218–222 (1989).

Inagaki, N., Fujita, S. and Satoh, K., Purification and properties of a thylakoidal enzyme of spinach involved in the processing of D1 protein of PS II reaction center, Current research in photosynthesis, M. Baltsvhffsky, Editor, Kluwer Academic Publishers: vol. III, pp: 763–766 (1990).

Inagaki, N. et al. Carboxyl–terminal processing protease for D1 precursor protein in spinach in Photosynthesis: from light to biosphere, P. Mathis, Editor, Kluwer Academic Publishers: vol. III, pp: 783–786 (1995).

Keiler, K.C., Waller, P.R.H. and Sauer, R.T., Role of a Peptide Tagging System in Degradation of Proteins Synthesized from Damaged Messenger RNA, Science 271: pp: 990–993 (1996).

Silber, K.R., Sauer, R.T., Deletion of the prc (tsp) gene provides evidence for additional tail–specific proteolytic activity in *Escherichia coli* K–12, Mol. Gen. Genet 242: pp: 237–240 (1994).

Taguchi, F. et al., Recognition signal for the C–terminal processing protease of D1 precursor protein in the photosystem II reaction center, FEBS Letters 326: pp: 227–231 (1993).

Takahashi, Y. et al., Genetic engineering of the processing site of D1 precursor protein of photosystem II reaction center in *Chlamydomonas reinhardtii*, Plant Cell Physiology 37: pp: 161–168 (1996).

Taylor, M.A., Packer, J.C.L. and Bowyer, J.R., Processing of the D1 polypeptide of the photosystem II reaction center and photoactivation of a low fluorescence mutant (LF–1) of *Scenedesmus obliquus*, FEBS Letters 237: pp: 229–233 (1988).

Takahashi, Y. et al., Chromatographic Purification and Determination of the Carboxy–Terminal Sequences of Photosystem II Reaction Center Proteins, D1 and D2, Plant Cell Physiology 31(2): pp: 273–280 (1990).

Krafft et al., Fluorescent Chemosensors for Ion and Molecule Recognition, 183–95, 1993.

Beebe et al., A Continuous Fluorimetric Assay for Tail–specific Protease, Academic Press, 51–56, 1998.

FIG. 5

```
1                                                                    50
..........  ..........  ..........  ..........  ..........
MHSRTNCLQT  SVRAPQPHFR  PFTAVKTCRQ  RCSTTAAAAK  RDQAQEQQPW
                        mature N-terminus           A
51                              ↓                                   100
..........  ..........  .......VTS  EQLLFLEAWR  AVDRAYVDKS
IQVGLGLAAA  ATAVAVGLGA  AALPAQAVTS  EQLLFLEAWR  AVDRAYVDKS 101                                                                 150
FNGQSWFKLR  ETY.......  ..........  ..........  ..........
FNGQSWFKLR  ETYLKKEPMD  RRAQTYDAIR  KLLAVLDDPF  TRFLEPSRLA 151                                                                 200
....GTAGSV  TGVGLEITYD  GGSG......  ..........  ..........
ALRRGTAGSV  TGVGLEITYD  GGSGKDVVVL  TPAPGGPAEK  AGARAGDVIV         770 bp 201                                                                 250
........GL  SLYDVSDLLQ  GEADSQVEVV  LHAPGAPSNT  R.........
TVDGTAVKGL  SLYDVSDLLQ  GEADSQVEVV  LHAPGAPSNT  RTLQLTRQKV 251                                                                 300
..........  ..........  ..........  .LATFNSNTT  AAAQQAFTEL
TINPVTFTTC  SNVAAAALPP  GAAKQQLGYV  RLATFNSNTT  AAAQQAFTEL
                                                            B
301
S.........  ..........  ..........  ..........  ......DIYS
SKQGVAGLVL  DIRNNGGGLF  PAGVNVARML  VDRGDLVLIA  DSQGIRDIYS LF-1 mutation
351                                                                 400
ADGNSIDSAT  PLVVLVNR..  ..........  ......↓...  ........LI
ADGNSIDSAT  PLVVLVNRGT  ASASEVLAGA  LKDSKRGLIA  GERTFGKGLI
                                          AS*

401                                                                 450
QTVVDLSD..  ..........  .........I  GVSPDVQLDP  EVLPTDLEGV
QTVVDLSDGS  GVAVTVARYQ  TPAGVDINKI  GVSPDVQLDP  EVLPTDLEGV 451             465
CR........  ....        SEQ. ID No: 21
CRVLGSDAAP  RLFG*       SEQ. ID No: 22
```

FIG. 6

```
Scenedesmus   CTG AAG GAC AGC AAG CGG GGC CTC ATA GCT GGC GAG CGC ACC TTT GGC AAG GGC CTC ATT     SEQ.ID No: 23
Wild Type     Leu Lys Asp Ser Lys Arg Gly Leu Ile Ala Gly Glu Arg Thr Phe Gly Lys Gly Leu Ile    SEQ.ID No: 24

LF-1          CTG AAG GAC AGC AAG CGG( )CC TCA TAG CTG GCG AGC GCA CCT TTG GCA AGG GCC TCA TT     SEQ.ID No: 25
Mutant        Leu Lys Asp Ser Lys Arg  Ala Ser End                                                SEQ.ID No: 26
                                      ↓
LF-1          CTG AAG GAC AGC AAG CGG( )CC TCATTA GCT GGC GAG CGC ACC TTT GGC AAG GGC CTC ATT    SEQ.ID No: 27
Revertant     Leu Lys Asp Ser Lys Arg  Ala SerLeu Ala Gly Glu Arg Thr Phe Gly Lys Gly Leu Ile    SEQ.ID No: 28
```

METHODS FOR IDENTIFYING HERBICIDAL AGENTS THAT INHIBIT D1 PROTEASE

This is a Continuation-In-Part application, filed under 37 CFR 1.153(b) and claiming priority to U.S. Ser. No. 09/173,281, filed Oct. 15, 1998, which is a continuation of U.S. Ser. No. 08/759,581, filed Aug. 4, 1998, now abandoned.

FIELD OF INVENTION

The present invention relates to the field of molecular biology and, in particular, to a method to identify a new herbicidal target, D1 protease, necessary for the processing of the D1 protein found in the photosystem II reaction center of all higher plants. The invention further relates to methods for identifying herbicidal agents that will inhibit D1 protease, and methods and genes useful for the recombinant production of D1 protease.

BACKGROUND

The Photosystem II (PSII) reaction center contains two homologous polypeptides, D1 and D2, that are responsible for the coordination of the primary photoreactants [Satoh, K. (1993) in *The Photosynthetic Reaction Center* (Deisenhofer, J. and Norris, J. R., eds.) Vol. I, pp. 289–318, Academic Press, New York; Seibert, M. (1993) in *The Photosynthetic Reaction Center* (Deisenhofer, J. and Norris, J. R., eds.) Vol. I, pp. 319–356, Academic Press, New York]. The D1 polypeptide of PSII is present in all organisms that use oxygenic photosynthesis to fuel metabolism. The source of electrons for the electron transport chain of oxygenic photosynthetic organisms is water. The oxidation of water to molecular oxygen occurs on a tetranuclear manganese cluster that is thought to be associated with the D1 polypeptide [Nixon et al., *Biochem.* 31, 10859–10871 (1992)].

D1 is expressed in precursor form [Grebanier et al., *J. Cell Biol.*, 78, 734, (1978); Reisfeld et al., *Eur. J. Biochem.*, 124, 125, (1992); Minami, J. B. and Watanabe, A. *Plant. Cell Physiol.* 26, 839–846 (1985)], inserted into the thylakoid membrane, and processed at its C-terminus [Marder et al., *J. Biol. Chem.* 259, 3900–3908 (1984); Diner et al., *J. Biol. Chem.* 263, 8972–8980 (1988); Nixon et al., *Biochem.* 31, 10859–10871 (1992)]. In cyanobacteria 16 residues are cleaved from precursor D1 (pre-D1) [Nixon et al., (1992), supra] whereas 9 residues are cleaved in higher plants (Takahashi et al., *FEBS Lett.* 240, 6–8 (1988); Takahashi et al., *Plant Cell Physiol.* 31, 273–280 (1990)), with processing occurring in all cases at the carboxy side of D1-Ala344. It has been suggested that this processing is effected by a protease enzyme, D1 protease.

Failure to process the carboxy-terminal extension of pre-D1 results in the inability to fully assemble the manganese cluster necessary for photosynthetic water oxidation [Diner et al., *J. Biol. Chem.* 263, 8972–8980 (1988); Taylor et al., *FEBS Lett.* 235, 109–116 (1988)]. As the oxidation of water is absolutely essential to photosynthesis, prevention of this process prevents photoautotrophic growth of all cyanobacteria, algae and higher plants. Agents that inhibit the C-terminal processing of the D1 protein represent herbicidal candidates.

Although several proteins termed "D1 protease" as well as genes ostensibly encoding D1 protease enzymes have been isolated from cyanobacteria, algae, and higher plants, there is no evidence until now that these enzymes are responsible for in vivo C-terminal processing of the D1 polypeptide. For example, Shestakov et al. [*J. Biol. Chem.* 269, 19354–19359 (1994)] and Anbudurai et al. [*Proc. Natl. Acad. Sci., USA* 91, 8082–8086 (1994)] teach the isolation of the ctpA gene from the cyanobacterium Synechocystis, a mutation which impairs the C-terminal processing of the pre-D 1. The characterization of this gene as encoding a D1 protease was made on the basis of the impairment, measured in vivo of pre-D1 processing in vivo and not on the basis of enzyme activity since no protein associated with this gene has as yet been isolated. Further studies by Applicants have shown, however, that the inactivation of the ctpA gene does not completely remove the ability of the mutant strain to process D1, suggesting that this protein is not wholly responsible for D1 processing.

An enzyme demonstrating D1 protease activity in vitro has been isolated from spinach [Fujita et al., *Plant Cell Physiol.* 36(7) 1169–1177 (1995)] and the gene encoding the enzyme has been cloned and sequenced [Inagaki et al., *Plant Mol. Biol.*, 30(1), 39–50 (1996)]. In vitro assays have shown that the spinach enzyme is capable of using a C-terminal fragment of the pre-D1 protein (consisting of 24 amino acids) as a substrate, but there has been no demonstration of a link between this enzyme and the in vivo processing of the pre-D1 protein [Taguchi et al., *J. Biol. Chem.*, 270(18), 10711–16 (1995)].

Pre-D1 protein processing activities have been isolated and partially purified from Scenedesmus and Pisum, [Packer et al., *Curr. Res. Photosynth., Proc. Int. Conf. Photosynth.*, 8th (1990), Meeting Date 1989, Volume 3, 759–62. Editor (s): Baltscheffsky, Margareta. Publisher: Kluwer, Dordrecht, Neth.] and from maize [Magnin et al., *Res. Photosynth., Proc. Int. Congr. Photosynth.*, 9th (1992), Volume 2, 211–14. Editor(s): Murata, Norio. Publisher: Kluwer, Dordrecht, Neth.]. These enzymes demonstrated activity in an in vitro PSII particle assay; however, no demonstration of in vivo activity of these enzymes has been obtained until now.

Isolation of an enzyme from a plant that has pre-D1 processing activity is not de facto evidence that it is indeed responsible for in vivo pre-D1 protein processing. For example, an enzyme contained in periplasmic lysates of *E. coli* tail-specific protease has been identified [Silber et al., *Proc. Natl. Acad. Sci., USA* 89, 295–299 (1992); Hara et al., *J. Bacteriol.* 173, 4799–4813 (1991)] that has about 30% identity to the putative D1 protease. Further, an enzymatic activity has been isolated by the Applicants from periplasmic isolates which has pre-D1 protein processing activity in vitro. While it is probable that these are one and the same enzyme, *E. coli* does not contain D1 and does not perform oxygenic photosynthesis. Therefore, it cannot be concluded that an enzyme is D1 protease purely on the basis of its homology to known D1 protease-encoding genes and evidence of in vitro activity.

Thus, in order to develop a method for the screening of herbicidal agents that target D1 protease, one problem to be solved is to positively identify the enzyme that is responsible for in vivo processing of the pre-D1 protein.

Methods for assaying the presence of pre-D1 protein processing activity are known. For example, Hunt et al., [*Res. Photosynth., Proc. Int. Congr. Photosynth.*, 9th (1992), Volume 2, 207–10. Editor(s): Murata, Norio. Publisher: Kluwer, Dordrecht, Neth.] teach an assay system using a truncated peptide substrate based on the C-terminal region of the D1 protein. Similarly, Packer et al., (*Curr. Res. Photosynth., Proc. Int. Conf. Photosynth., supra*) describe an assay using PSII thylakoid particles from the Scendedesmus D1 protease-deficient mutant LF-1. LF-1 PSII particles are incubated with a solution extracted from sonicated wildtype Scenedesmus thylakoids and D1 is processed to its normal mature size where the Mn complex is then photoligated and the photooxidation of water is detected. Finally, Taguchi et al., [*J. Biol. Chem.*, 270(18), 10711–16 (1995)] teach an assay method using purified spinach D1 protease and either in vitro truncated D1 protein or synthetic oligopeptides, both containing the D1 C-terminus as a substrate. Enzyme products are identified by gel shift analysis and HPLC, respectively.

Although assay methods such as these are useful for the detection of pre-D1 processing activity, they are not readily adaptable for commercially useful high throughput screens because they use large quantities of enzyme, rely on identification of enzyme substrate by either gel or HPLC analyis, and take hours to give results. Additionally, assays using truncated D1 as substrates (Hunt et al., supra; Taguchi et al., supra) must run the assay at a pH higher than that at which the enzyme functions in vivo.

Another problem to be solved then is to develop an assay system that is facile and adaptable to high through-put screening.

SUMMARY OF THE INVENTION

The invention provides an in vitro method for identifying a herbicidal agent which inhibits D1 protease comprising: a) incubating an effective amount of a D1 protease in a sample suspected of containing a herbicidal agent with a suitable D1 enzyme substrate wherein an enzyme product is formed; and b) detecting and quantifying the enzyme product formed.

The invention further provides an in vivo method for detecting a herbicidal agent which inhibits D1 protease comprising
(a) incubating a reaction mixture containing
  (i) a wildtype cell having (A) an active D1 protease enzyme capable of processing a D1 pre-protein; and (B) a Photosystem II core complex capable of variable fluorescence; (ii) a suspected herbicidal agent which inhibits D1 protease; and (iii) suitable growth medium for a time sufficient to permit D1 turnover; then
(b) illuminating the reaction mixture at illumination conditions of about $200\mu$ Einsteins.m$^{-2}$.s$^{-1}$ for a time sufficient to permit D1 turnover; and
(c) measuring variable chlorophyll fluorescence produced in step (b), whereby the level of the variable chlorophyll fluorescence is correlated with the herbicidal activity of the suspected herbicidal agent. In a further embodiment of the in vivo detection method, the reaction mixture may also contain a mutant cell containing an inactive D1 protease enzyme characterized by an inability to process a D1 pre-protein and a Photosystem II core complex capable of variable chlorophyll fluorescence. This mutant cell is used as a control and is preferably LF-1 Scenedesmus.

It is further within the scope of the invention to provide a method for the recombinant production of D1 protease enzyme comprising: (a) transforming a suitable host cell with a vector comprising a gene encoding a D1 protease enzyme, the gene operably connected to suitable regulatory sequences; (b) growing the transformed cell under conditions wherein D1 protease is expressed; and (c) recovering the expressed D1 protease.

The invention further provides genes encoding D1 protease enzymes which encode the amino acid sequences of SEQ ID NOS:4, 9, 13, and 15 wherein the amino acid sequences may encompass amino acid substitutions, deletions or additions that do not alter the function of the D1 protease.

Additionally, the invention provides a method for the detection of a D1 protease enzyme comprising: (i) contacting a derivatized D1 protease substrate with a D1 protease enzyme to form a reaction mixture, the derivatized D1 protease substrate comprising (a) a fluorophore; and (b) a quenching moiety; and (ii) incubating the reaction mixture of step (i) under conditions that permit D1 processing; (iii) detecting the processed D1 substrate of step (ii) by a fluorescence detection means.

The invention additionally provides a derivatized D1 protease substrate as given in Formula I:

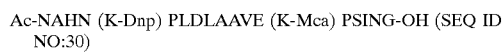
Ac-NAHN (K-Dnp) PLDLAAVE (K-Mca) PSING-OH (SEQ ID NO:30)

wherein:
K-Mca is lysine derivatized in its ε position with 7-methoxycoumarin-4-acetic acid;
K-Dnp is lysine derivatized in its ε position with 2,4-dinitrophenol; and
Ac is an acetyl group.

BRIEF DESCRIPTION OF THE FIGURES, BIOLOGICAL DEPOSITS, AND SEQUENCE LISTING

FIG. 5 shows a composite diagram of primer locations and amplification products used to clone and sequence the Scenedesmus D1 protease gene.

FIG. 6 shows the translated nucleotide sequence for a 60 base region of the D1 protease gene from three strains of Scenedesmus.

Figure 1:
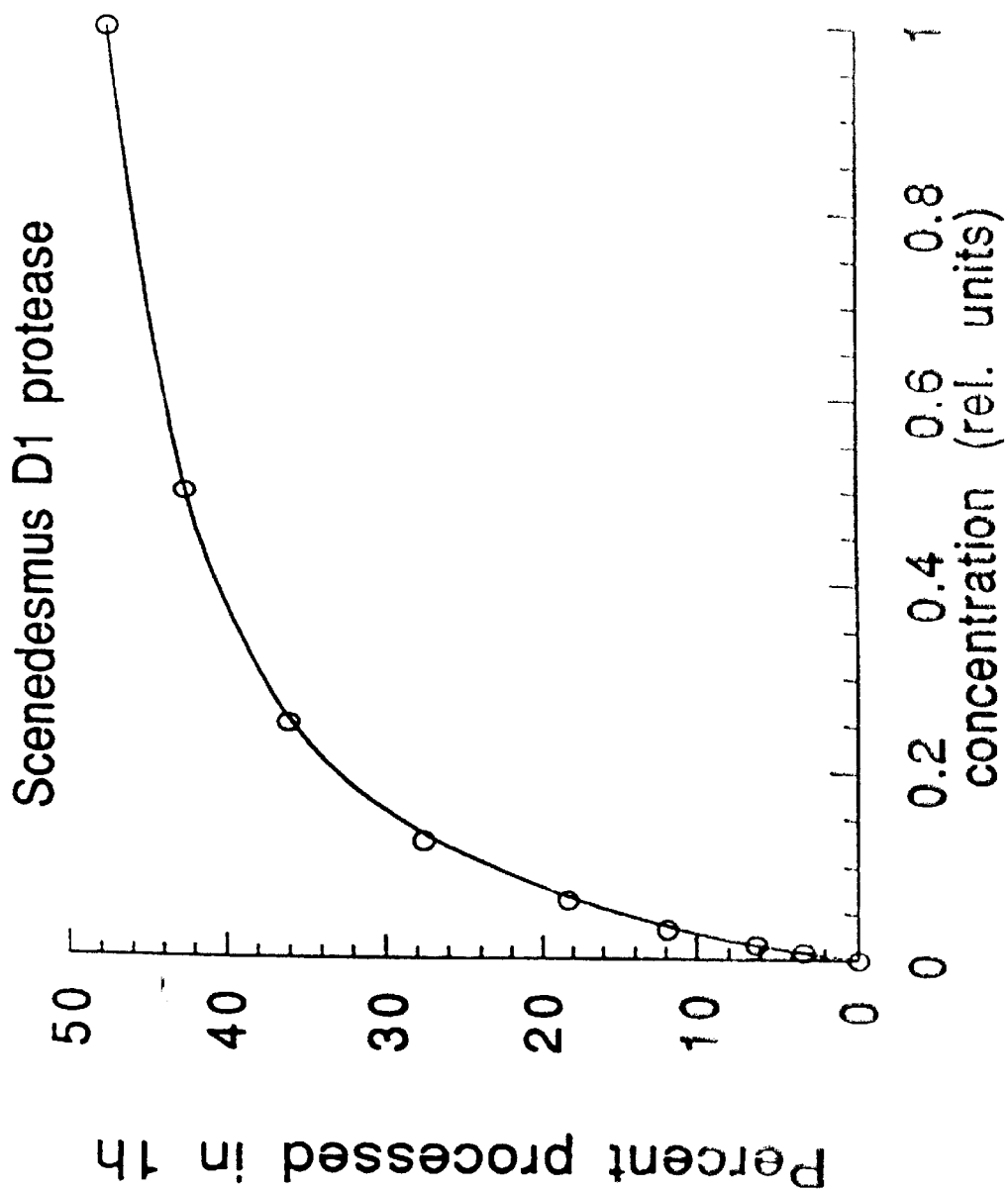
FIG. 1 is a plot of Scenedesmus D1 protease enzyme activity versus enzyme concentration.

Applicants have made the following biological deposit under the terms of the the Budapest Treaty on the International Recognition of the Deposit of Micro-organisms for the Purposes of Patent Procedure:

| Depositor Identification Reference | Int'l Depository Designation | Date of Deposit |
|---|---|---|
| *Escherichia coli* THSD1P containing the wheat D1 protease gene | ATCC 98186 | 26 September 1996 |

As used herein, "ATCC" refers to the American Type Culture Collection international depository located at 10801 University Boulevard, Manassas, Va. 20110-2209 U.S.A. The "ATCC No." is the accession number to cultures on deposit with the ATCC.

Applicant(s) have provided 29 sequence listings in conformity with 37 C.F.R. 1.821–1.825 and Appendices A and B ("Requirements for Application Disclosures Containing Nucleotides and/or Amino Acid Sequences") and in conformity with "Rules for the Standard Representation of Nucleotide and Amino Acid Sequences in Patent Applications" and Annexes I and II to the Decision of the President of the EPO, published in Supplement No. 2 to OJ EPO, December 1992.

DETAILED DESCRIPTION OF THE INVENTION

Applicants have identified a novel herbicide target, D1 protease, and realized the use of purified D1 protease from recombinant and native sources in assay systems to identify herbicidal agents targeting D1 protease. These methods will facilitate the development of new products by the agricultural industry and have the potential for increasing the current understanding of the mechanisms by which the Photosystem II core complex (PS II) reaction center performs its photosynthetic functions. Applicants are the first to isolate and purify a pre-D1 processing enzyme and demonstrate that the enzyme has both in vitro and in vivo functionality. Applicants have purified the D1 protease enzyme to homogeneity from the alga, *Scenedesmus obliquus*, cloned the gene on the basis of amino acid sequence, identified conserved residues that likely correspond to the active site of the enzyme, and have shown that a mutation in this gene results in the loss of in vivo D1 protease activity.

Applicants have developed an ELISA immunoassay that uses unprocessed D1 included in the thylakoid membranes or PSII core complexes isolated from the LF-1 mutant of Scenedesmus as substrates. Processing is detected by the progressive appearance of the mature C-terminus of the D1 protein that is specifically recognized by an antibody. This assay is fast, automatable, allows for multiple assays to be run simultaneously, uses amounts of enzyme in the 10 femtomolar range and, in the case of thylakoid membranes, may be operated at physiological pH (i.e., about pH 4–6), similar to that found for the in vivo D1 processing system.

A method for the recombinant production of D1 protease has also been developed. Although the gene encoding spinach D1 protease has been isolated previously, to date there is no report of recombinant production of this enzyme by others.

Expression of recombinant D1 protease proceeded first by the isolation and purification of the enzyme from a suitable source, amino acid sequencing, synthesis of appropriate PCR primers based on the amino acid sequence, amplification of cDNA, cloning and isolation of the gene, and insertion of the gene into suitable expression vectors for the transformation and expression of the gene in recombinant hosts.

As used herein the following terms may be used for interpretation of the claims and specification.

7-methoxycoumarin-4-acetic acid will be abbreviated as "Mca".

2,4-dintrophenol will be abbreviated as "Dnp".

"Ac" is an acetyl group.

"Gene" refers to a nucleic acid fragment that expresses a specific protein, including regulatory sequences preceding (5' non-coding) and following (3' non-coding) the coding region.

"Chimeric" gene refers to a gene comprising heterogeneous regulatory and coding sequences.

A "foreign" gene refers to a gene not normally found in the host organism but that is instead introduced by gene transfer techniques.

"Coding sequence" refers to a DNA sequence that codes for a specific protein and excludes the non-coding sequences.

As used herein, suitable "regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. These regulatory sequences include promoters, translation leader sequences, transcription termination sequences, and polyadenylation sequences.

"Promotor" refers to a DNA sequence in a gene, usually upstream (5') to its coding sequence, which controls the expression of the coding sequence by providing the recognition for RNA polymerase and other factors required for proper transcription. A promotor may also contain DNA sequences that are involved in the binding of protein factors which control the effectiveness of transcription initiation in response to physiological or developmental conditions.

"Constitutive promotors" refers to those promoters that direct gene expression in all tissues and at all times.

"Inducible promotors" refer to those promotors which turn on the description of a gene in the presence of an inducer.

The term "operably linked" refers to nucleic acid sequences on a single nucleic acid molecule which are associated so that the function of one is affected by the other. For example, a promoter is operably linked with a structural gene when it is capable of affecting the expression of that structural gene (i.e., that the structural gene is under the transcriptional control of the promoter).

The term "expression" refers to the production of the protein product encoded by a gene.

The terms "protein" and "polypeptide" will be used interchangeably.

The terms "D1 pre-protein", "D1 pre-polypeptide", and "pre-D1" refer to the D1 precursor protein that has been N-terminally processed but contains an additional 8 to 16 amino acid residues at the C-terminal portion of the protein which are cleaved off by D1 protease at the carboxy side of D1-Ala344 to yield the mature D1 protein.

The terms "D1 protein", "D1 polypeptide", and "mature D1 protein or polypeptide" refer to an electron transport polypeptide that is both N- and C-terminally processed and a subunit of the PSII reaction center. This polypeptide is implicated in coordinating a tetranuclear manganese (Mn) cluster which is found in the PSII reaction center of all photosynthetic organisms and is responsible for the coordination of the primary photoreactants. The term "psbA" refers to the gene encoding the D1 protein.

The term "PSII core complex" refers to a multisubunit pigment-protein complex that consists of a PSII reaction center complex and two light-harvesting chlorophyll-proteins (CP47 and CP43).

The term "D1 protease" refers to an enzyme responsible for the processing of the D1 pre-protein at the C-terminal end for the production of the mature D1 polypeptide.

The terms "C-terminal tail" and "C-terminal tail fragment" refer to that portion of the C-terminal end of the D1 pre-protein that is cleaved off by D1 protease. The C-terminal tail fragment may comprise from about 8 to about 16 amino acid residues depending on the species from which it is isolated.

The terms "Photosystem II reaction center", "photosystem II", and "PSII" refer to a multisubunit pigment-protein complex in the thylakoid membrane in the chloroplasts of higher plants, algae, and in cyanobacteria. The Photosystem II reaction center contains the D1 polypeptide. A general review of the properties of PSII maybe found in Vermaas et al., *Cell Cult. Somatic Cell Genet. Plants* (1991), Volume 7B, 25–111. Editor(s): Bogorad, Lawrence; Vasil, Indra K. Publisher: Academic Press, San Diego, Calif.

The term "D1 turnover" refers to the degradation, biosynthesis, and reincorporation of D1 into the PSII reaction center.

The term "RACE" refers to rapid amplification of cDNA ends and describes a process used in the art of molecular biology to amplify either end of a target cDNA from a cDNA population. The RACE method is fully described in the EXAMPLES.

As used herein "Fv" means the variable fluorescence yield of chlorophyll emitted by PSII where fluorescence yield is determined by the redox state of the primary quinone electron acceptor, Qa.

The term "Fo" refers to the lower limit of variable fluorescence (Fv) when Qa is fully oxidized.

The term "Fm" refers to the upper limit of variable fluorescence (Fv) when Qa is fully reduced.

The term "Fi" refers to Fv detected by the first photons absorbed or weak light illumination following dark adaptation.

The term "weak light illumination" refers to $\leq 0.1$ photon per sec per center.

The term "Qa" will refer to the the primary quinone electron acceptor for photosystem II.

The term "fluorescence detection means" refers to any method of measuring fluorescent light emitted from a reaction system. A fluorescence detection means typical in the art is a fluorescent spectrophotometer such as the Cytofluor Series 4000 multi-well fluorescence plate reader.

"Transformation" herein refers to the transfer of a foreign gene into the genome of a host organism or cell and its genetically stable inheritance.

The term "plasmid" or "vector" as used herein refers to an extra chromosomal element often carrying genes which are not part of the central metabolism of the cell, and usually in the form of circular double-stranded DNA molecules.

The term "restriction endonuclease" refers to an enzyme which binds and cuts within a specific nucleotide sequence within double-stranded DNA.

"Host cell" means the cell that is transformed with the introduced genetic material.

Methods of Screening for Herbicidal Agents

The invention provides methods of screening for compounds and agents that possess herbicidal activity by specifically interfering with the D1 protease. These assays may take a variety of formats but all rely on detecting the effective C-terminal processing of a pre-D1 or a pre-D1 fragment. The assays developed include an ELISA-based method as well as various methods adaptable for a high-throughput screen of compounds.

Assay Reagents

All assays used a variety of reagents including D1 protease, a D1 protease substrate, a primary antibody having binding affinity for the enzyme product, and an enzyme reporter conjugated to the antibody. Optionally, a secondary antibody may be used having binding affinity for the primary antibody. The enzyme reporter may be conjugated to either the secondary or primary antibody depending on the assay format.

Source of D1 Protease

It is contemplated that any higher plant, algal or cyanobacterial organism that performs oxygenic photosynthesis will contain functional D1 protease to process D1 of the Photosystem II reaction center. D1 protease may be isolated from any such source for use in assay systems or to isolate genes useful for recombinant expression of the protein.

Potential sources of D1 protease include, but are not limited to, soybean, rapeseed, sunflower, cotton, corn, tobacco, alfalfa, wheat, barley, oats, sorghum, rice, cruciferous vegetables, broccoli, cauliflower, cabbage, parsnips, tomato, potato, spinach, alfalfa, sorghum, hardwood and softwood trees, forage grasses, as well as from algae, and cyanobacteria. The D1 protease will possess the ability to process the D1 pre-protein at the C-terminal end for the production of the mature D1 polypeptide. D1 protease may be isolated from natural sources or be produced recombinantly as described herein.

Preferred in the present assays is D1 protease isolated from spinach, wheat, tobacco, algae, and cyanobacteria.

Isolation and Purification of the D1 Enzyme

The D1 protease may be isolated from plant tissue using a series of chromatographic and separation techniques useful for the purification of proteins [See, for example, Berot et al., *Proteines Veg.* (1985), 335–472 Publisher: Tech. Doc. Lavoisier, Paris, France.]

Isolated and purified spinach D1 protease is known [Fujita et al., *Plant Cell Physiol.*, 36(7), 1169–77 (1995)] from extracts of sonicated spinach thylakoids using a series of chromatographic systems including chromatography on quaternary aminoethyl anion-exchange, hydroxylapatite, copper-chelating affinity and gel-filtration columns.

D1 protease was purified from wheat, the algae Scenedesmus, and the cyobacterium Synechocystis PCC 6803 by isolating the thylakoid membranes containing the PSII reaction center and subsequent purification by Hydroxylapatite, Hydrophobic Interaction, MonoQ ion exchange, Isoelectric Focusing, and gel filtration chromatography.

Confirmation of Applicants' isolation of D1 protease was made on the basis of the demonstration of pre-D1 processing activity as determined by both in vivo and in vitro assays.

Cloning and Sequencing

N-terminal sequencing was performed on tryptic digests of purified wheat or algal protease. Methods for amino acid sequencing are known in the art [See, for example, Hunkapiller et al. (*Front. Biochem. Biophys. Stud. Proteins Membr.*, Proc. Int. Conf. (1983), Meeting Date 1982, 23–36. Editor(s): Liu, Teh-Yung. Publisher: Elsevier, New York, N.Y.) for a general review of Edman degradation, and Kasarda (U.S. Agric. Res. Serv., North Cent. Reg., Rep. (1976), ARS-NC-40, 175–80) for an example of amino acid sequencing of wheat proteins].

Amino acid sequence was used to design degenerate primers for the PCR amplification of cDNA (U.S. Pat. Nos. 4,683,202; 4,683,195). Total mRNA was extracted from the plant or algal tissue using methods well known in the art [Sambrook et al., Molecular Cloning: A Laboratory Manual, Second Edition (1989) Cold Spring Harbor Laboratory Press] and the Oligo dT-primer cDNA was synthesized. Depending on the primers used, amplification of the cDNA gave either partial or full length PCR products from Scenedesmus and wheat as determined by gel electrophoresis. Full length cDNA amplification products were sequenced using well known base sequencing techniques [Branza-Nichita, Norica, *Stud. Cercet. Biochim.*, 38(1–2), 49–56 (1995); Cantor et al., *Mass Spectrom. Biol. Sci.* (1996), 519–33. Editor(s): Burlingame, A. L.; Carr, Steven A. Publisher: Humana, Totowa, N.J.] and inserted into suitable transformation vectors for expression.

Host Cells

Suitable host cells for the recombinant production of D1 protease may be either prokaryotic or eukaryotic and the selection of a suitable host cell will be limited only by its ability to express an active enzyme. Preferred cells will be those typically useful for over-expression of foreign proteins such as *E. coli*, Bacillus, Klebsiella, fungi (e.g., Aspergillus), insects and yeasts (e.g., Pichia, Hansenula and Saccharomyces). *E. coli* is the most preferred host.

Growth Conditions

Cells used in the present invention include preferred host bacterial cells (for recombinant expression of D1 protease) and leaves, algal cells and cyanobacteria cells (for enzyme purification and D1 protease assays).

Growth conditions for all cell types used are commonly available and well known in the art. Typically bacterial cells are grown at 30° C. in appropriate media. Preferred growth media in the present invention are common commercially prepared media such as Luria Bertani (LB) broth, or Sabouraud Dextrose (SD) broth.

Suitable media used for Scenedesmus and Synechocystis was NGY medium [Bishop, *Methods Enzymol.* 23, 372–408 (1971)] and BG11 (Ripka et al., *J. Gen. Microbiol.* (1979) 111, 1–61 respectively, although any media that will support the growth and metabolism of the particular organism(s) sought to be grown will suffice.

Other defined or synthetic growth media may also be used and the appropriate medium for growth of the particular organism will be known by one of ordinary skill in the art of microbiology or fermentation science.

Suitable pH ranges for the cultures are between pH 5.0 to pH 9.0 where pH 6.0 to pH 8.0 is preferred as the initial condition.

Vectors

The present invention provides a variety of plasmids or vectors suitable for the cloning and transformation of the D1 protease enzyme into a suitable host cell. Suitable vectors will be those which are compatible with the host cell employed. Suitable vectors can be derived, for example, from a bacteria, a virus (such as bacteriophage T7 or a M-13 derived phage), a cosmid, a yeast or a plant. Protocols for obtaining and using such vectors are known to those of ordinary skill in the art [Sambrook et al., Molecular Cloning: A Laboratory Manual—volumes 1, 2, 3 (Cold Spring Harbor Laboratory: Cold Spring Harbor, N.Y., 1989)].

Typically, the vector contains sequences directing transcription and translation of the protease gene, a selectable marker, and sequences allowing autonomous replication or chromosomal integration. Suitable vectors comprise a region 5' of the gene which harbors transcriptional initiation controls, and a region 3' of the DNA fragment which controls transcriptional termination. It is most preferred when both control regions are derived from genes homologous to the transformed host cell although it is to be understood that such control regions need not be derived from the genes native to the specific species chosen as a production host.

Initiation control regions, or promoters, which are useful to drive expression of the D1 protease gene in the desired host cell are numerous and familiar to those of ordinary skill in the art. Virtually any promoter capable of driving the gene encoding the desired protein is suitable for the present invention. The T7 promoter is preferred. Termination control regions may also be derived from various genes native to the preferred hosts. Optionally, a termination site may be unnecessary, however, it is most preferred if included.

For intracellular production of the desired protein, DNA encoding the protein is linked operably through its initiation codon to the selected expression control region such that expression results in the formation of the appropriate messenger RNA. Alternatively, if production of a fusion protein is desired, DNA encoding for the desired protein is linked at its 5' end to the 3' end of the gene encoding the carrier protein. Optionally, the reverse orientation could be constructed where DNA encoding the carrier protein is linked at its 5' end to the 3' end of the DNA encoding the desired protein. Also, if desired, DNA coding for an enzyme-cleavable site may be incorporated without reading frame disruption, between the DNA encoding the desired protein and the carrier-encoding DNA, so that expression yields a fusion protein from which the desired protein can be liberated by proteolytic enzyme cleavage. An example of the fusion protein approach to protein production is provided by Contreras et al., [*Bio Technology,* 9, 378 (1991)].

Preferred within the context of the present invention are commercially available vectors such as pET-32 vector (Novagen, Madison, Wis.).

Transformation and Expression of D1 Protease

Once suitable vectors are constructed they are used to transform the desired host cells. Introduction of the gene cassette containing the D1 protease gene into *E. coli* may be accomplished by known procedures such as by transformation, e.g., using calcium-permeabilized cells, electroporation, or by transfection using a recombinant phage virus [Sambrook et al., supra].

The pET-32 vector containing the D1 protease gene from wheat was used to transform *E. coli* BL21 (DE3)pLysS competent cells according to standard protocols. Expression of the gene was monitored by determining the intensity of the corresponding stained band following SDS-PAGE.

Enzyme Substrates

Suitable enzyme substrates for D1 protease may be isolated from a variety of plant sources provided that D1 processing is prevented. Suitable plant sources include, but are not limited to, higher plants such as soybean, rapeseed, sunflower, cotton, corn, tobacco, alfalfa, wheat, barley, oats, sorghum, rice, cruciferous vegetables, broccoli, cauliflower, cabbage, parsnips, tomato, potato, spinach, alfalfa, sorghum, hardwood and softwood trees, forage grasses, as well as from algae and cyanobacteria. The preferred source for use in the present invention is mutant LF-1 Scenedesmus cells, possessing a mutant, non-functional D1 protease. The substrate may be purified D1 pre-protein, may be partially purified, or may be used as contained within the thylakoid membrane or within a PSII core complex. Additionally, the substrate may be a synthetic peptide or peptide analogue (1a) containing a portion of the D1 pre-protein comprising the processing site. Alternatively, the substrate may be produced recombinantly via the expression of partial or full length genes coding for some part of the D1 polypeptide.

At least for higher plant D1 protease, the enzyme assay can be performed at physiological pH (pH 4–5) only when the thyalkoid membrane containing D1 pre-protein is used as the enzyme substrate.

Antibodies

In a preferred embodiment of the assay, antibodies were directed to a synthetic peptide comprising the final 16 residues of all known mature D1 polypeptides. The peptide was conjugated to a carrier protein and antibodies were raised in rabbits according to standard methods (see, for example, Hayes et al., *Methods Enzymol.,* 187:116–24 (1990)).

Antibodies can be either primary, having affinity for the enzyme product, or secondary, having affinity for the primary antibody, depending on the assay format.

Either primary or secondary antibodies may be linked to a reporter enzyme. A variety of reporter enzymes may be used. For example, suitable reporter enzymes include, but are not limited to, hydrolases, lyases, oxidoreductases, transferases, isomerases and ligases. Others are peroxidase, glucose oxidase, phosphatase, esterase and glycosidase. Specific examples include alkaline phosphatase, lipases, beta-galactosidase, horseradish peroxidase and porcine liver esterase. Preferred in the instant invention are alkaline phosphatase (AP) and horseradish peroxidase (HRP).

In embodiments where enzymes serve as reporters the substrate/enzyme reaction forms a product which results in a detectable signal, typically a change in color, fluorescence or chemiluminescence. In many cases chromogenic substances are an additional requirement for the color reaction. Chromogenic reagents are chosen on the basis of the reporter enzyme used. Some typical enzyme/chromogen pairs include, but are not limited to, β-galactosidase with potassium ferrocyanide or potassium ferricyanide; horseradish peroxidase with 3,3' diaminobenzidine (DAB); Glucose oxidase with NBT; and alkaline phosphotase with NBT and 5-bromo-4-chloro-3-indolylphosphate-4-toluidine (BCIP) or p-nitrophenylphosphate (PNPP). Methods for the use of chromatogenic substance with enzyme reactions are well known in the art and are fully described by Tijssen [Practice and Theory of Enzyme Immunoassays in Laboratory Techniques in *Biochemistry and Molecular Biology.,* eds., R. H. Burton and P. H. Van Knippenberg, (1988)].

Similarly, an example of an enzyme/substrate combination that produces a fluorescent signal is the enzyme alkaline phosphatase and the substrate Attophos [JBL Scientific Inc., San Luispo, Calif.] or HRP and N-acetyl-3,7-dihydroxyphenoxazine [Molecular Probes, Inc., Eugene, Oreg.].

An example of an enzyme/substrate combination that produces a chemiluminescent signal is the enzyme HRP and the BM Chemiluminescence ELISA Reagent substrate [Boehringer Mannheim Corp., Indianapolis, Ind.].

Preparation of an antibody-enzyme reporter conjugate may be accomplished using methods well known to those skilled in the art. Suitable examples are found in Williams [*J. Immun. Methods,* 79, 261 (1984)].

Assay Formats

In one embodiment, an ELISA format was used to assay for D1 protease. D1 protease was purified from Scenedesmus and the enzyme substrate consisted of a PSII core complex containing D1 pre-protein. Substrate cores were linked to a multi-well (96-well) microtiter plate; D1 protease was added to the wells for a fixed time period and product was analyzed by using the primary antibody (having binding affinity for the enzyme product) followed by a secondary antibody (having binding affinity for the primary antibody). The quantity of primary antibody attached to the product of the D1 protease reaction was detected through an enzyme linkage to the secondary antibody and the enzyme activity was measured colorimetrically to quantify D1 protease activity. Optionally, a primary antibody was prepared which was conjugated to an enzyme reporter, eliminating the need for the secondary antibody.

This method fits the standard ELISA immunoassay format as detailed by Omesso [*Lab.* 2000, 9(8), 52–6 (1995)].

In an alternate embodiment, assay methods have been developed to detect different enzyme products. For example, the action of D1 protease on the D1 pre-protein generates a mature D1 protein and a C-terminal tail fragment. Applicants have developed assay methods to detect both of these products independently.

In Applicants' assay for the detection of the mature protein, enzyme substrate was provided in the form of thylakoid membranes containing D1 pre-protein, for example, isolated from Scenedesmus LF1 mutant cells and D1 protease isolated and purified from wheat leaves. The assay was conducted in microtiter plate wells, being modified to include a permeable membrane that facilitated the separation of the enzyme reaction products. In this assay, mature D1 protein was detected using either a double (primary, secondary) antibody system or a single antibody having affinity for the mature protein and linked to an enzyme reporter.

Applicants also developed an assay to detect the C-terminal tail enzyme product. Cleavage of the C-terminal tail from the D1 pre-protein results in a free C-terminal tail having a reactive primary amine group. Various molecular probes are known which react with primary amines and may be used for peptide labeling. Examples of such molecular probes include but are not limited to fluorescamine [Stein et al., *Fluorescence News* (1973), 7(2), 9–10 (1973)]; ATTO-TAG [Molecular Probes, Inc., Eugene, Oreg.]; naphthalenedialdehyde/cyanide [Lunte et al., *Curr. Sep.,* 10(1), 19–25 (1990)]; 3-(4-carboxybenzoyl)-2-quinolinecarboxaldehyde [Liu et al., *Anal. Chem.,* 63(5), 408–12 (1991)]; isothiocyanate compounds [Stobaugh et al., U.S. Pat, No. 4,891,323); 3-Benzoyl-2-quinolinecarboxaldehyde [Beale et al., *Talanta,* 36(1–2), 321–5 (1989)]; o-phthalaldehyde [Benson et al., *Proc. Natl. Acad. Sci. U. S. A.,* 72(2), 619–22 (1975)]; and ninhydrin [Udenfriend, U.S. Pat. No. 3,689,221). Preferred molecular probes within the context of the present invention are fluorescamine and ATTO-TAG.

The assay for the C-terminal tail enzyme product proceeds in a similar fashion to the assay for the mature protein, using thylakoid membranes and microtiter plates modified with the Durapore® membrane, except that the fluorescent molecular probe is reacted with the solution containing the cleaved C-terminal tail. An increase in fluorescence in this sample is an indication of D1 protease activity.

In another embodiment, Applicants developed an assay system utilizing live algal or plant tissue for the detection of D1 protease activity. In a preferred embodiment wildtype Scenedesmus cells are used in the assay system. The wildtype cells have a normal, functional D1 protease and therefore process D1 pre-protein normally.

The assay relies on the use of chlorophyll fluorescence yield (Fv) as an indicator of the extent of pre-D1 processing. The presence of an inhibitor in the assay system blocks processing and gives rise to a higher Fv at low light intensity (Fi), and a lower Fv at high light intensity, as compared to the uninhibited wildtype used as a control.

Additionally, the assay system may be designed to incorporate the LF-1 mutant Scenedesmus (which lacks the ability to process the D1 pre-protein) as a control. In this format the wildtype and mutant cells are used together in the assay system. Mutant cells have no D1 processing ability due to a defective D1 protease and thus show a lower Fv than that of the wildtype under strong illumination [Metz et al., *Biochem. Biophys. Res. Comm.* 94, 560–566 (1980)]. Another advantage to the use of LF-1 mutants as a control is that the Fi of LF-1 cell is 2–3 fold higher than that of the wildtype cell. Thus, when wildtype cells or cells from higher plants (i.e., duck weed) are illuminated for several hours in a suitable growth medium containing D1 protease inhibitor, an increase in Fi and a decrease in Fv is seen when measured at light intensity of 10–100 photons per sec per center.

An alternate embodiment of the invention is suggested by the construction of a deletion mutant of Synechocystis 6803 (S) [Nixon et al., *Biochemistry* 31 (1992) 10859–10871] which lacks the three copies of the psbA gene encoding the D1 polypeptide. S, incorporates into the Photosystem II reaction center a copy of the D1 polypeptide in which the last sixteen amino acid residues are missing. This polypeptide is therefore expressed in a form that in wild type only appears upon processing of the last sixteen residues by D1 protease. Despite the absence of the sixteen residue carboxy-terminal extension, this strain is able to grow photosynthetically (doubling time 20 h) and to evolve oxygen (200 $\mu$mole $O_2 \cdot$(mg of $Chl^{-1}) \cdot h^{-1}$) at rates close to those of wild type.

The availability of the S strain makes possible an in vivo assay for inhibitors that are specific for D1 protease. The assay consists of growing the wild type and the S strains side by side under photoautotrophic growth conditions (light intensity 30–50 $\mu E \cdot m^{-2} \cdot s^{-1}$) and in the presence and absence of the inhibitor to be tested. The increase in cell density is measured at 730 nm as a function of time to determine the rate of cell growth. In the wild type strain, an inhibitor specific for D1 protease would block the C-terminal processing of the precursor form of the D1 polypeptide, thereby preventing assembly of the manganese cluster necessary for photosynthetic electron transport. Growth of the wild type strain would cease. In contrast, this inhibitor would have no effect on the growth rate of the S strain, which does not require D1 protease activity as the D1 polypeptide already lacks the C-terminal extension, the absence of which still allows photosynthetic growth. An inhibitor, not specific for D1 protease, would inhibit growth of both the wild type and S strains.

In an alternate embodiment the present invention provides an assay based on the quenching of fluorescent moieties. The assay uses a fluorescence donor/quencher system incorporated into the D1 protease substrate. The substrate is prepared where an amino acid on one side of the D1 processing site is derivatitized to allow for the incorporation of a fluorophore. Similarly, another amino acid on the opposite side the processing site is derivatized to allow for the incorporation of a quenching moiety. The reaction conditions for D1 processing are typically at a temperature of about 20° C. to about 30° C., where a temperature of about 25° C. is suitable. Incubations may take place over a time period of about 20 minutes to about 90 minutes. The assay may be run at a pH of between 5.5 to about 7.0 and will accommodate a range of about 12–25 uM substrate and about 350 to about 700 ug of enzyme. Fluorescence donor/quencher systems are well known in the art (see for example Krafft et al., ACS Symp. Ser. (1993), 538 (Fluorescent Chemosensors for Ion and Molecule Recognition), 183–95, for a review of the use of fluorescent probes in the detection of protease enzymes). The assay proceeds by the incubation of the derivatized substrate in the presence of D1 protease. Cleavage of the sissile substrate bond in between the elements of the fluorescence donor/quencher system produces an increase in the fluorescence yield which can be correlated with enzyme activity.

One system used commonly in polypeptide analysis is EDANS (5-(2-Aminoethylamino)-1-naphthalenesulfonic acid) and DABCYL (4-[[4'-(dimethyl-amino)phenyl]azo] benzoic acid). This particular system has been used with success for the assay of tail specific protease (Beebe et al., *Anal. Biochem.* (1998), 263(1), 51–56,); for the measurement of renin activity (Wang et al., *Anal. Biochem.* (1993), 210(2), 351–9) and the assay of retroviral proteases (U.S. Pat. Nos. 5,011,910; 5,164,300). Other systems are well known in the art. Preferred in the present invention is the combination of 2,4-dintrophenol and 7-methoxycoumarin-4-acetic acid.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Restriction enzyme digestions, phosphorylations, ligations and transformations were done as described in Sambrook, J. et al., Molecular Cloning: A Laboratory Manual, Second Edition (1989) Cold Spring Harbor Laboratory Press.

The meaning of abbreviations is as follows: "h" means hour(s), "min" means minute(s), "sec" means second(s), "d" means day(s), and "L" means liter.

Algal and Plant Strains as Source of D1 Protease

The algal strains used in this study were the wildtype of *Scenedesmus obliquus,* strain $D_3$, and a non-photosynthetic low-fluorescent mutant (LF-1) derived from wildtype by X-ray mutagenesis [Metz et al., *Biochem. Biophys. Res. Comm.* 94:560–566 (1980)]. A photoautotrophic suppressor strain, derived from LF-1 (LF-1-RVT-1) [Bishop, (1983) *In The Oxyven Evolving System of Photosynthesis.* (Y. Inoue et al., eds.) pp. 177–187, Academic Press, New York], was also examined. All strains were kindly provided by Norman Bishop (Oregon State University, Corvallis, Oreg.). Except where fermentors were used the cells were grown in 20 L carboys on NGY medium (Bishop, *Methods Enzymol.* 23:372–408 (1971)) in the light at 25° C.

Wheat plant tissue was obtained from wheat leaves *Triticum aestivum,* var. Fidel.

Cyanobacterium Synechocystis Strain PCC6803 was obtained from the Pasteur Culture Collection, Institut Pasteur, Paris, France.

Purification of D1 Protease from Scenedesmus Membrane Extracts

Membranes containing D1 protease were extracted from wildtype cells of *Scenedesmus obliquus* tissue. Cells were suspended in 1 volume per weight of 20 mM HEPES-KOH, 10 mM KCl, 10% glycerol, and pH 7.25 (Buffer H) and centrifuged 5 min at 5000 rpm (4200×g) in a GS-3 rotor. The pelleted cells were resuspended in 1 volume per weight in buffer H and stored at –80° C. until use. For a typical protease isolation, 1 L of cell suspension was thawed and processed through a microfluidizer (model 110Y; Microfluidics Corporation, Newton, Mass.) by using 4 passes (18–23, 000 psi) with cooling in a wet ice bath between passes. The homogenate was centrifuged 10 min at 10,000 rpm (16,000× g) in a Sorvall GSA rotor (Newtown, Conn.) to remove cell debris. The pellet was washed with buffer H to resuspend sedimented thylakoids and was added to the supernatant. The combined slurry was homogenized by stirring 30 min or by using a Teflon™/glass homogenizer. Thylakoids were collected by centrifuging 2 h (or overnight) in Beckman 45 Ti rotors at 45,000 rpm (235,000×g). The pelleted thylakoids were resuspended in buffer H by using a Teflon™/glass homogenizer and brought to a concentration of 2 mg chlorophyll/mL and 0.5% by volume TRITON X-100 from a 20% aqueous stock. After stirring for 30 min, the thylakoids were centrifuged for 2 h at 45,000 rpm (235,000×g) in a 45 Ti rotor. The TRITON X-100 supernatant was collected and stored on wet ice. The thylakoid pellet was resuspended in buffer H and brought to 2 mg/mL chlorophyll and 0.5% TRITON X-100. After stirring 30 min, it was centrifuged 2 h in a 45 Ti rotor at 45,000 rpm (235,000×g).

Hydroxylanatite Purification

The second TRITON X-100 supernatant was combined with the first and loaded onto a 5×35 cm column of hydroxylapatite (Fast flow, Calbiochem, San Diego, Calif.) that had been previously equilibrated with 10 mM $K_2HPO_4/KH_2PO_4$, pH 7.0, 10% glycerol. After loading (10 mL/min), the column was washed with 500 mL of equilibration buffer and 250-mL fractions were collected. This was followed by 1 L of 100 mM $K_2HPO_4/KH_2PO_4$, pH 7.0 and 10% glycerol and 50-mL fractions were collected and assayed. Fractions showing D1 protease activity were concentrated and submitted to hydrophobic interaction chromatography.

Hydrophobic Interaction Purification

The hydrophobic interaction column (TSK-Gel Phenyl-5PW, 20 mm ID×15 cm, TosoHaas) was preceded by a guard column of the same material (20 mm ID×2 cm). The column was first washed at 3 mL/min for 20–30 min with buffer B (20 mM HEPES-KOH, pH 7.25 and 20% glycerol) and then equilibrated at 10° C. with 60% Buffer A (20 mM HEPES-KOH, pH 7.25 and 20% glycerol plus 2 M $(NH_4)_2SO_4$): 40% Buffer B at the same flow rate for 30–40 min. The sample was loaded onto the hydrophobic interaction column at 3 mL/min by using a Pharmacia Superloop. A linear gradient was then applied at 3 mL/min which went from 60%A:40%B to 20%A: 80%B over the next 90 min. The run was completed by ramping up to 100%B over the following 20 min and maintained at that level for another 15 min. Three mL fractions were collected. Active fractions from the hydrophobic interaction column were pooled and concentrated by using a Centriprep 10 (Amicon) to 23 mL and passed through an Econo-Pac 10DG desalting column (Bio Rad, Melville, N.Y.) previously equilibrated with Buffer B and used according to the manufacturer's instructions.

Ion-Exchange Purification

The approximate 4 mL sample was then loaded onto an HR10/10 MonoQ column (Pharmacia, Pisscataway, N.J.) at a flow rate of 1 mL/min, previously equilibrated with Buffer B. The column was subsequently washed for 10 min with 100% Buffer B followed by a linear gradient from 100% Buffer B to 100% Buffer C (Buffer B plus 0.5 M NaCl) over a period of 100 min and maintained at 100% Buffer C for 10 min, all at a flow rate of 1 mL/min. Two-mL fractions were collected and assayed. Active fractions were concentrated and submitted to isolectric focusing purification.

Isoelectric Focusing Purification

Preparative isoelectric focusing was carried out in a BioRad Rotofer cell using 45 mL of 20% glycerol, 0.1% CHAPS (3-[(3-cholamidopropyl)-dimethyl ammonio]-1-propane-sulfonate), 1% Servalyte 4–6 and 0.25% Servalyte 3–10. The cell was prerun for 1 h at 12 W to establish the pH gradient and following the addition of 4 mL of sample to the center well subsequently run for 3–4 h at 5° C. at 12 W. The enzyme migrated with an isoelectric point of 5.0±0.1. The fractions were collected and assayed. Active fractions were concentrated and submitted to gel-filtration chromatography.

Gel-Filtration Purification

The Rotofer fractions were concentrated to about 50 μL by using a Centricon™ 10 (Amicon) and injected onto a TSK-Gel G4000SWXL column (8 μm particle size, 7.8 mm ID×60 cm) previously equilibrated with Buffer D (Buffer B plus 100 mM NaCl). The column was run at 0.25 mL/min and 0.5 mL fractions were collected. Aliquots of each fraction were diluted 1:4 or 1:6 with Buffer B and assayed. The peak of activity appeared at about 92 min from the start of the run. A comparison with the elution times of a collection of standard proteins, run under the same conditions, gave an estimated molecular mass that ranged from 36–42 kDa. This agrees favorably with a molecular mass of 42±1 kDa based on SDS-PAGE (FIG. 3) and a calculated [Genetics Computer Group (1994) In Program Manual for the Wisconsin Package, Version 8, Genetics Computer Group, Madison, Wis.] mass of 40,578 Da, based on the translated sequence of mature D1 protease (SEQ ID NO:4) from Scenedesmus.

Purification of D1 Protease from Wheat

The purification of D1 protease from wheat followed essentially the same protocol as described above with the exception that the wheat chloroplasts were suspended in a hypotonic buffer (10 mM HEPES-NaOH, pH 7.3), and then the thylakoid membranes were isolated by centrifugation. The membranes were resuspended in 20 mM HEPES, 10% glycerol, pH 7.25, at 1 mg chlorophyll/mL. 0.5% TRITON X-100 was added to extract the D1 protease from the membrane.

The wheat purification differed from the above protocol at the hydroxylapatite stage where, after loading the sample onto the column, the column was first washed with 200 mL of 50 mM Pi-buffer (pH 7.0). It was then eluted with a 500 mL linear gradient from 50 to 150 mM Pi-buffer/10% glycerol (DA 7.0). The column was further washed with 150 mM Pi-buffer and the eluents were collected by fraction collector (12 mL/fraction), and each fraction was assayed for D1 protease activity.

The protocol for wheat differed from the above procedure also at the ion-exchange purification stage where the following elution protocol was used:

| Time (min) | Solvent A (20 mM HEPES/20% glyercol, pH 7.25) | Solvent B (A + 0.5 M NaCl) |
|---|---|---|
| 0 | 100% | 0% |
| 10 | 100% | 0% |
| 10.01 | 80% | 20% |
| 40 | 80% | 20% |
| 130 | 40% | 60% |
| 130.1 | 0% | 100% |
| 140 | 0% | 100% |

Finally, the gel filtration step was expanded to include a second gel filtration where, after the first gel filtration column step (TSK-Gel, G4000SWXL), the sample was further purified using a TSK-Gel G2000SWXL column. The conditions used for this step are the same as used for the first gel filtration column.

Purification of D1 Protease from Synechocystis 6803

D1 protease was isolated from thylakoid membrane of Synechocystis 6803 in a similar manner to the protocol used for purifying wheat D1 protease described above. The thylakoid membranes were isolated from the Synechocystis cells as described in Tang et al. [*Biochemistry*, 33, 4594–4603 (1994)].

Figure 3:
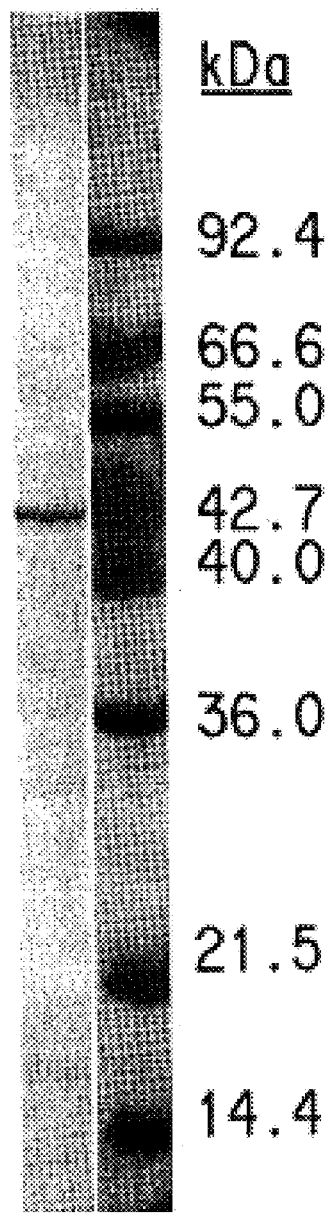
FIG. 3 is a gel showing the migration as a single band of D1 protease from Scenedesmus following the complete purification procedure.

All of the above column purification steps were performed at 4–10° C. The yields of the various steps and their respective specific activities are listed in Tables 1–3 below. Purification to homogeneity was confirmed by a protein blot as shown in FIG. 3, where a single band identified as D1 protease is seen to migrate at 42.7 kD.

TABLE 1

SUMMARY OF THE PURIFICATION OF D1 PROTEASE FROM 500G OF *SCENEDESMUS OBLIQUUS* CELLS

| Step | Activity (rel. units) | Protein | Specific Activity (rel. units) |
|---|---|---|---|
| Membrane extract | nd | 1 g | nd |
| Hydroxylapatite pooled fractions | 168,000 | 210 mg | 800 |
| Hydrophobic Interaction pooled fractions | 49,000 | 20 mg | 2,440 |
| MonoQ pooled fractions | 52,000 | 1.1 mg | 46,000 |
| Isoelectric Focusing pooled fractions | 15,600 | nd | nd |
| Gel filtration pooled fractions | 9,100 | 5–10 $\mu$g | $0.9–1.8 \times 10^6$ | nd = not determined

TABLE 2

SUMMARY OF THE PURIFICATION OF D1 PROTEASE FROM 500G OF WHEAT LEAVES

| Step | Activity (rel. units) | Protein | Specific Activity (rel. units) |
|---|---|---|---|
| Membrane extract | nd | 2 g | nd |
| Hydroxylapatite pooled fractions | 890,000 | 130 mg | 6,846 |
| Hydrophobic interaction poole fractions | 170,400 | 12 mg | 14,200 |
| MonoQ pooled fractions | 112,000 | 500 $\mu$g | 224,000 |
| First gel filtration (TSK-Gel G4000SWXL) pooled fractions | 96,000 | 70 $\mu$g | $1.4 \times 10^6$ |
| Second gel filtration (TSK-Gel G2000SWXL) | 90,000 | 10 $\mu$g | $9.2 \times 10^6$ | nd = not determined

TABLE 3

SUMMARY OF THE PURIFICATION OF D1 PROTEASE FROM 500G OF CYANOBACTERIUM SYNECHOCYSTIS CELLS

| Step | Activity (rel. units) | Protein | Specific Activity (rel. units) |
|---|---|---|---|
| Membrane extract | nd | 3.5 g | nd |
| Hydroxylapatite pooled fractions | 339,000 | 240 mg | 1,412 |
| Hydrophobic interaction pooled fractions | 53,238 | 10 mg | 5,324 |
| MonoQ pooled fractions | 42,820 | 400 $\mu$g | 107,050 |
| First gel filtration (TSK-Gel G4000SWXL) pooled fractions | 29,600 | 90 $\mu$g | $3.3 \times 10^5$ |
| Second gel filtration (TSK-Gel G2000SWXL) | 19,200 | 21 $\mu$g | $9.1 \times 10^5$ | nd = not determined

Example 1

Cloning and Sequencing of the D1 Protease Gene from Scenedesmus

Preparation of Purified Enzyme for Amino Acid Sequencing

D1 protease was biochemically isolated from Scenedesmus as described above and prepared for amino acid sequencing.

Figure 4:
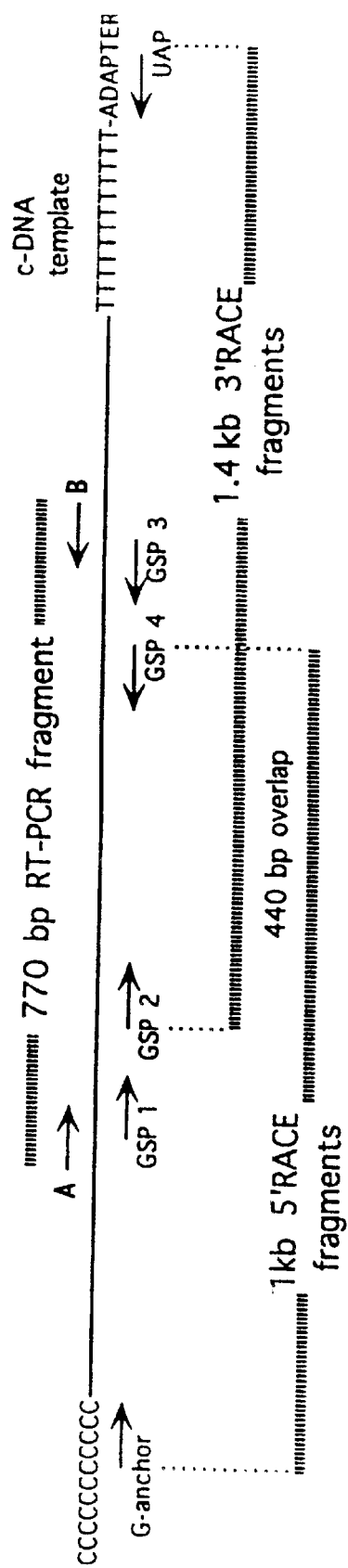
FIG. 4 shows an alignment of tryptic fragments with full length translated D1 protease gene from Scenedesmus.

SDS-PAGE and blotting were carried out according to a protocol [Best et al., (1994) In Techniques in Protein Chemistry, Vol. V, pp. 565–574, Academic Press, New York) established by the Wistar Protein Microchemistry Laboratory (Philadelphia, Pa.)]. A 12% polyacrylamide gel (30:1.8 w/w, acrylamide:bisacrylamide) 1.5 mm thick was poured, polymerized and left to stand overnight at room temperature prior to use. SDS-PAGE was run according to Best et al. [supra] with the upper buffer chamber containing 0.2% SDS and 0.1 mM thioglycolate. The solubilizing buffer (2×) contained 0.2 M sucrose, 6% SDS, 125 mM Tris, 4 mM EDTA, 0.04% bromphenol blue and 2% b-mercaptoethanol (v/v) adjusted to pH 6.9. This solution was added to an equal volume of concentrated protease solution and loaded onto the sample well of the polyacrylamide gel. The gel was run overnight at room temperature. The gel was then soaked for 25 min in Transfer Buffer composed of 10×Towbin buffer (250 mM Tris, 1.92 M glycine)+400 mL MeOH diluted to 4 L with Milli-Q water. BioRad TransBlot PVDF membrane (0.2 $\mu$m) was soaked for 10 sec in methanol and then for 20 min in Transfer Buffer. Blotting was carried out in a BioRad liquid Trans-Blot Cell using the above indicated Transfer Buffer and according to the manufacturer's instructions. A current of 240 mA was applied for 3 h at room temperature. The blot was washed three times for 5 min each with Milli-Q water and then stained for 1 min with 0.1% Amido Black in 10% acetic acid in Milli-Q water. The blot was destained for 1 min with 5% aqueous acetic acid and washed thoroughly with Milli-Q water. The blot was air-dried and sent to the Wistar Protein Microchemistry Laboratory, Philadelphia, Pa., for sequencing. Tryptic digest of the protein on the blot and subsequent HPLC purification of the tryptic fragments were performed as described in Laemmli [*Nature*, 227680–685 (1970)]. Degradative Edman sequencing was conducted at both the N-terminus and on selected HPLC purified tryptic fragments. In the latter case the MALDI (Matrix Assisted Laser Desorption Ionizaton) mass spectra were also obtained on the sequenced fragments as a confirmation of the sequence calls. The amino acid sequences obtained are shown in FIG. 4. The various tryptic fragments for which amino acid sequence data were obtained are shown aligned with the translated full-length D1 protease sequence. The mature amino terminus is noted, as is the site of the LF-1 mutation. The resultant LF-1 amino acid sequence is shown below the wildtype sequence (an asterisk denotes a stop codon). Horizontal arrows show the location of degenerate primers used to recover the initial 770 bp fragment of the gene.

Isolation of Nucleic Acid

Total RNA was extracted from Scenedesmus by the following procedure: 35 g of frozen cell paste was ground with 80 mL of buffer G (8 M guanidine HCl, 20 mM EDTA, 20 mM MES pH 7.0 and 50 mM $\beta$-mercaptoethanol) in a PowerGen 125 tissue homogenizer (Fisher Scientific Pittsburgh, Pa.) for 60 sec set on high. The homogenate was extracted with 150 mL phenol/chloroform/isoamyl alcohol (25:24:1), and then spun in a Sorvall GSA rotor for 45 min at 8000 rpm (10,400×g) at 25° C. The supernatant was recovered and the RNA precipitated with 0.2 volumes of 1 M acetic acid and 0.7 volumes of ethanol while at −20° C., overnight. The RNA was pelleted by centrifuging in a GSA rotor at 10,000 rpm (16,300×g) for 15 min at 4° C. The pellet was washed twice with 10 mL of 3 M sodium acetate, pH 5.2, with a final rinse of 15 mL of 70% ethanol. The pellet was resuspended in 4 mL of RNAse-free water and stored at −70° C. until use. Poly-A containing messenger RNA was recovered from undiluted total RNA using the PolyATract system from Promega (Madison, Wis.), according to the manufacturer's instructions. The integrity of the RNA was confirmed by running on a 1% Tris-acetate agarose gel.

Total chromosomal DNA was recovered from Scenedesmus by the following procedure: about 500 mg of cells were harvested from the surface of agar plates, and resuspended in 500 µL of TSE (5 mM Tris-HCl pH 8.5, 50 mM NaCl, and 5 mM EDTA). The resuspended cells were frozen dropwise in liquid nitrogen, then ground while frozen by using a mortar and pestle. Ground cells were suspended in 1.4 mL TSE, 40 µL proteinase K (2.5 mg/mL), 100 µL 20% SDS, and 100 µL 20% Sarkosyl. The mixture was incubated at 65° C. for 2 h, then extracted with 2 mL buffer-saturated phenol, and centrifuged for 15 min at 6,000 rpm (9400×g) in a Sorvall HS-4 rotor. The supernatant was extracted with 2 mL chloroform and spun as above. The nucleic acids were precipitated from the extracted supernatant with 0.1 volume of 3 M sodium acetate, and an equal volume of isopropanol. The precipitate was pelleted by spinning at 6000 rpm (9400×g) for 20 min in the HS-4 rotor, then dried, and resuspended in 900 µL TE (10 mM Tris-HCl pH 7.5, 1 mM EDTA) in microfuge tubes. RNA was digested with 20 units RNase-it (Stratagene, La Jolla, Calif.). Starches were removed by adding 300 µL of 7.8 M ammonium acetate and centrifuging 30 min at 12,000×g. The DNA was precipitated by adding 1.8 mL isopropanol and centrifuging 30 min at 12,000×g. The DNA was resuspended in 1 mL TE. Typical concentrations were 400 µg/mL.

Cloning and Sequencing

The HPLC purified tryptic peptides of the D1 protease were sequenced as described above and were ordered by matching them to translated D1 protease genes from wheat. Degenerate oligonucleotide primers "A" (SEQ ID NO:1) and "B" (SEQ ID NO:2) were designed to prime regions of minimum degeneracy within the peptide fragments shown in FIG. 5. Primers A and B were degenerate primers based on sequenced tryptic peptide fragments shown in FIG. 6. The resulting 770 bp RT-PCR gene fragment yielded nucleotide sequence data used to design gene specific primers GSP-1, 2,3 and 4. For 5'RACE, cDNA was oligo-dC-tailed and the first round of PCR performed with the G-anchor primer and GSP-3. The second round of PCR used the G-anchor primer and GSP-4. For 3'RACE, cDNA synthesis was primed with a special oligo-dT adapter primer which contains a region complementary to the Universal Amplification Primer (UAP). The first round of amplification was primed with UAP and GSP-1, the second round was primed with UAP and GSP-2. The spacing of the primers predicted a PCR (Polymerase Chain Reaction) product of about 770 bp.

Oligo dT-primed cDNA was prepared from Scenedesmus polyA mRNA by using a BRL SuperScript preamplification system from Gibco BRL (catalog no. 18089-011, Life Technologies, Inc., Gaithersburg, Md.). This cDNA was used as template for a PCR primed with degenerate oligonucleotides "A" and "B". The amplification employed a "touchdown" cycle sequence (Don et al., *Nucleic Acids Res.* 19, 4008 (1991)] with the annealing temperature dropping by 2 degrees every 3 cycles, from 60° C. to 50° C., followed by 15 cycles at 47° C. The reaction product was electrophoresed in a Tris-acetate low-melting point agarose gel, and a faint band of about 770 bp was excised from the gel. The gel was melted at 70° C. and a 10 µL aliquot used as template in an identical repeat amplification reaction, except that a 30 min incubation at 72° C. was included to enhance the 3' addition of single deoxyadenosines by Taq™ polymerase (Hoffman-LaRoche, Ltd., Basel, Switzerland). This second amplification reaction produced a concentrated band of DNA that was excised from a low melt gel and ligated directly into a pGEM-T vector (Promega, Madison, Wis.), according to the supplier's instructions.

Clones containing inserts of the expected 770 bp size were sequenced on an ABI 377 automated sequencer (Applied Biosystems, Foster City, Calif.). The nucleotide sequences of the cloned fragments permitted the design of exact gene-specific primers. The primers were then used for the Rapid Amplification of cDNA Ends (RACE) in conjunction with a 5'RACE kit (Cat. No. 18373-019) and a 3'RACE kit (cat. no. 18374-025) both from Gibco BRL, and used according to the manufacturer's instructions, except for the substitution of Expand High Fidelity polymerase (Boehringer Mannheim, Indianapolis, Ind.) in place of Taq™ polymerase (Hoffman-LaRoche, Ltd.). Reaction products were run on low melt agarose gels. The 5'RACE procedure produced an amplified DNA product that was 1 kb in length. The 3'RACE procedure yielded a product that was 1.4 kb in length. Both bands were excised. As the Expand High Fidelity polymerase generates blunt-ended fragments, the following step was included to add single deoxyadenosine tails. Twenty µL aliquots of each band were incubated at 72° C. for 30 min in the presence of 10 mM Tris-HCl, pH 8.3, 50 mM KCl, 1.5 mM MgCl$_2$, 0.33 mM dATP, and 0.5 units Taq™ polymerase (Hoffman-LaRoche, Ltd.). The tailed fragments were then ligated into a pGEM-T vector.

A minimum of 4 independent clones were sequenced (both strands) for each of the 5'RACE and 3'RACE products of the LF-1 and wildtype cDNAs. Clones from the 5' end overlapped clones from the 3' end by 440 bases. Sequencing was performed as above, and the data managed using the Lasergene SeqMan program (DNASTAR Inc., Madison, Wis.). Multiple independent clones were sequenced as a precaution against mutations introduced during the course of DNA amplification. Applicants reasoned that a true mutation, present in LF-1, would appear in all LF-1 clones and none of the wildtype clones, whereas amplification mutants would appear randomly. A mutation rate of 1 error per 2000 bases sequenced was still observed despite the use of a "high fidelity" polymerase.

Once the nucleotide sequence difference between the D1 protease genes of LF-1 and wildtype was determined by sequencing the RACE clones, the mutation was verified in the Scenedesmus genome by PCR amplification and sequencing of the homologous region. Two µg each of chromosomal DNA from the wildtype, LF-1, and the suppressor strain, LF-1 RVT-1, were used as template. A pair of gene-specific primers 507 bp apart were used to prime the reaction, which used the "touchdown" cycle sequence method [Don et al., *Nucleic Acids Res.* 19(14):4008 (1991)]. The reaction products were run on a standard agarose gel, and the predominant band, running at 1200 bp, was excised. The fact that the genomic PCR product was 700 bp larger than expected indicates the presence of one of more introns. The DNA was recovered using GeneClean (Bio 101, La Jolla, Calif.), and sequenced as above using the same primers used for PCR. The sequence of the Scenedesmus D1 protease gene is given in SEQ ID NO:3 and the amino acid sequence of the encoded protein is given in SEQ ID NO:4.

Example 2

Comparison of Scenedesmus D1 Protease Amino Acid and Nucleotide Sequencing and Confirmation of in vivo Pre-D1 Processing The 5' end of the mRNA from wildtype was determined by sequencing 5'RACE clones. A total of 21 were sequenced, and the three longest showed a consistent startpoint. The remaining clones were shorter and had random startpoints, presumably the result of incomplete cDNA synthesis. The first in-frame methionine was designated the start codon.

Nucleotide sequencing of the wildtype Scenedesmus cDNA predicts a protein of 464 amino acids. Of these, the first 77 comprise a leader sequence as N-terminal amino acid sequencing of the mature protein indicated the first residue to be valine 78 (FIG. 4). A thylakoid transit sequence can be discerned with basic residues (Lys39 and Arg40), 39 and 38 residues, respectively, upstream from the mature N-terminus, followed by a region of hydrophobic residues and terminating in a typical AXA lumenal processing site [von Heijne et al., *Eur. J. Biochem.* 180, 535–545 (1989); Shackleton et al., *J. Biol. Chem.* 266, 12152–12156 (1991)]. Upstream of the transit sequence is a region, enriched in serines and threonines, that is characteristic of a chloroplast signal sequence (Gavel et al., *FEBS Lett.* 261, 455–458 (1990)).

Nucleotide sequencing of the cDNA isolated from the LF-1 mutant revealed a single base deletion in the glycine 387 codon that shifts the reading frame, causing a translation stop after 2 additional amino acids (FIG. 6). The circled lysine shown in FIG. 6 is a likely component of the active site of the protease. The parentheses show the site of the single G deletion in the LF-1 and revertant strains. An arrow identifies the site of a single T insertion in the LF-1 suppressor strain, LF-1-RVT-1.

The point mutation was confirmed in genomic DNA by using PCR to directly sequence a 500 bp region of the LF-1 mutant and wildtype genomes. In addition, the same region was sequenced from an LF-1 revertant strain (LF-1-RVT-1), which was shown to have a single base-pair insertion 7 bases downstream of the LF-1 deletion. This insertion restores the proper reading frame after two amino acids that differ from wildtype (FIG. 6).

Example 3

Cloning and Sequencing of the D1 Protease Gene from Wheat

Preparation of Purified Enzyme for Amino Acid Sequencing

D1 protease was biochemically isolated from wheat as described above and then prepared for amino acid sequencing. The purified enzyme was electrophoresed on SDS-PAGE according to Laenimli [(1970), supra]. The gel was stored for 24 h prior to use and 0.1 mM thioglycolate and 0.2% SDS was added to the running gel buffer. The protein was then transblotted to PVDF membrane in a BioRad Trans-Blot cell as described above and according to the manufacturer's instructions. The blot was stained with Amido Black and sent to the Wistar Microchemistry Core Facility, Philadelphia, Pa., for sequencing. The band containing the D1 protease band, was cut out of the blot. The protein band was digested with trypsin and the fragments separated on a C-18 HPLC column according to Best et al. [(1994, Techniques in Protein Chemistry V, pp. 565–574, Academic Press, New York]. Mass spectra and N-terminal sequence were performed on the cleanest and largest peptide fragments.

Isolation of Messenger RNA

Wheat leaves were harvested when plants were 15 cm tall, and 4 h after exposure to light. The leaves were cut with sterile scissors and immediately frozen in liquid nitrogen.

Total RNA was extracted from leaves by the following procedure: 35 g of crushed frozen leaves were ground with 80 mL of buffer G (8M guanidine HCl, 20 mM EDTA, 20 mM MES pH 7.0, 50 mM β-mercaptoethanol) in a Power-Gen 125 tissue homogenizer (Fisher Scientific) for 60 sec at high speed. The homogenate was extracted with 150 mL phenol/chloroform/isoamyl alcohol (25:24:1), and then spun in a Sorvall GSA rotor for 45 min at 8000 rpm at 25° C. The supernatant was recovered and the RNA precipitated with 0.2 volumes of 1 M acetic acid and 0.7 volumes of ethanol while at −20° C., overnight. The precipitate was pelleted by centrifuging 10,000 rpm, 15 min at 4° C. The pellet was washed twice with 10 mL of 3 M sodium acetate, pH 5.2, with a final rinse of 15 mL of 70% ethanol. The pellet was resuspended in 4 mL of RNAse-free water and stored at −70° C. until use. Poly-A containing messenger RNA was recovered from undiluted total RNA using the PolyATract system from Promega (Madison, Wis.), according to manufacturer's instructions. The integrity of the RNA was confirmed by running on a 1% Tris-acetate agarose gel.

Reverse Transcriiptase PCR

Complementary DNA was prepared for use as template for PCR. To accomplish this, wheat poly-A mRNA was primed with the "reverse" primer GCNCC(GA)TCNGCCTCATA, (SEQ ID NO:29) based on the amino acid sequence data. The bases in parenthesis are the alternative bases used in the degenerate primer. Complementary DNA was synthesized with Superscript reverse transcriptase from Gibco BRL, following the manufacturer's instructions. For the first PCR, the "forward" degenerate primer was ATGGA(CT)AT(CT)TA(CT)GA(CT)GC (SEQ ID NO:5) and the "reverse" primer as shown above. Each primer concentration was 166 pMoles per 50 uL reaction. The amplification employed a "touchdown" cycle sequence (Don et al., *Nucleic Acids Res.* 19(14):4008 (1991)] with the annealing temperature dropping by 2 degrees every 3 cycles, from 60° C. to 50° C., followed by 15 cycles at 47° C. The reaction product was electrophoresed in a Tris-acetate low-melting point agarose gel, and a faint band of about 400 bp was excised from the gel. The gel was melted at 70° C. and a 10 uL aliquot was used as template for a second PCR amplification, using the above forward primer and an internally nested reverse primer, GC(TGA)AT(CT)TC(GA)AT(TGC)CC(CT)TC (SEQ ID NO:6). The second amplification reaction produced a concentrated band of about 300 bp DNA that was excised from a low melt gel and ligated directly into a pGEM-T vector (Promega, Madison, Wis.) according to the supplier's instructions. The resulting clone was sequenced to provide data for design of primers used for rapid amplification of c-DNA ends (RACE) and mRNA capture.

The 3' end of the gene was cloned using a capture oligo strategy as follows. The biotinylated oligo (biotin-TCTGAACCTGGAATCTCACACATCCTTGA) (SEQ ID NO:7), based on the sequence of the above PCR clone and specific to the middle of the gene, was synthesized by the DuPont oligonucleotide facility (Wilmington, Del.). The biotinylated oligonucleotide was hybridized to total mRNA and then bound to streptavidin magnetic beads (Dynal International, Oslo, Norway). The captured mRNA was used to synthesize c-DNA primed by oligo dT. After second strand synthesis, the ends were tagged with single overhanging 3'deoxyadenosine residues by incubating with Taq™ polymerase (Hoffman-LaRoche, Basel, Switzerland). The tagged DNA was then ligated into a pGEM-T vector,as above. The ligated DNA was used to transform *E. coli*. Transformants were selected on LB agar plates containing Ampicillin and individual colonies were screened by gel electrophoresis for plasmids containing inserts. Inserts were identified by sequencing. An 850 bp fragment of the Wheat D1 protease gene was recovered. It contains the poly-A region, the stop codon and more than half of the coding region, and overlaps the 300 bp PCR clone by about 250 bases. The 5' end of the gene was recovered using a 5'RACE kit (Cat. No. 18373-019) from Gibco BRL, and used according to the manufacturer's instructions, except for the substitution of Expand High Fidelity polymerase (Boehringer Mannheim, Indianapolis, Ind.) in place of Taq™ polymerase.

The nucleotide sequence of the 5' and 3' clones was determined and combined to yield the complete sequence for the mature protease. The sequence of the wheat D1 protease gene is given in SEQ ID NO:8 and the amino acid sequence of the encoded protein is given in SEQ ID NO:9.

Example 4

Cloning and Sequencing of the D1 Protease Gene from Synechocystis 6803

Preparation of Purified Enzyme for Amino Acid Sequencing

D1 protease was biochemically isolated from Synechocystis 6803 as described above for Scenedesmus, Example 2, and the protein prepared for amino acid sequencing.

Cloning of the D1 Protease Gene ctpB

Degenerate primers were designed based on amino acid sequence data. The primers GG(TCG)GA(AG)GA(TC)TGGGT(GTC) SEQ ID NO:10 and AT(AG)TA(AGC)CCNACNAC(AG)TT(TC)TC SEQ ID NO:11 were used to generate a 600 bp PCR fragment using 25 cycles of 1 min 93° C., 1 min 55° C. and 30 sec 72° C. The fragment was ligated into a pGEM-T vector (Promega, Madison, Wis.), according to the supplier's instructions. The resulting construct was used to generate a "ctpB" gene probe for use in Southern mapping. Mapping was accomplished by digesting total Synechocystis 6803 DNA with various combinations of restriction enzymes and then separating the digested DNA by gel electrophoresis. The DNA was blotted to membranes and probed with the above construct. Analysis of the mapping data indicated that digestion of Synechocystis 6803 DNA with HindIII and Pst1 would produce a 3.2 kb fragment containing the "ctpB" gene. An enriched gene bank was created by cutting the 3.2 kb region out of HindIII-Pst1 digested DNA run on an agarose gel, and ligating the recovered DNA fragments into HindIII-Pst1 cut pBluescript vector (Stratagene, Madison, Wis.). The resulting ligation products were transformed into E. coli and plated for single colonies. Colony lifts were probed with "ctpB" gene probe to identify colonies containing the gene. Positive colonies contained the 3.2 kb HindIII-Pst1 fragment which was sequenced and found to include the entire "ctpB" gene as well as a portion of the FtsZ gene. The sequence of the Synechocystis 6803 D1 protease gene is given in SEQ ID NO:12 and the amino acid sequence of the encoded protein is given in SEQ ID NO:13.

Example 5

Isolation and Sequencing of the Gene Encoding Tobacco D1 Protease

A cDNA library was constructed from tobacco and was screened using a 770 bp fragment of the wheat D1 protease gene. Screening of the library resulted in the isolation of a 1994 bp DNA fragment. The sequence of this fragment is given in SEQ ID NO:14 and the encoded protein is given in SEQ ID NO:15. Confirmation that this sequence encodes an active D1 protease was determined by heterologous expression in E. coli and enzyme assay of the gene product.

Example 6

Transformation of E. coli with the Wheat D1 Protease Gene and Expression of Active D1 Protease Vector Construction and Expression PolyA mRNA was isolated from wheat as described above. cDNA was synthesized by using the materials and instructions provided in the Superscript Preamplification Kit (Life Technologies, Inc., Gaithersburg, Md.). Gene specific primers were designed to prime at the 5' mature end and the 3' end of the gene. To these were added, respectively, NcoI and BamHI sites.

```
CAG CCA TGG CGC TCA CGG AGG AGA AC    (SEQ ID NO:16)
    NcoI      5' mature end ATA CTT GGG ATC CAT ATC ACG           (SEQ ID NO:17)
  Stop     BamHI
```

The "touchdown" PCR program (see above) consisted of 1 min at 94° C., an annealing step of 1 min, and then 1 min at 72° C. The temperature of the annealing step was progressively lowered starting at 60° C. for 1 min (for 3 cycles) and then lowered by 2 degrees every three cycles until 50° C. was reached whereupon 5 cycles were performed. The PCR product was cut with the restriction enzymes, NcoI and BamHI, from Promega (Madison, Wis.). This fragment was then subcloned into a pET expression vector (pET-32a(+) (Novagen Inc., Madison, Wis.) that encodes the protease fused to thioredoxin, and a linker containing an enterokinase proteolytic cleavage site. The expression vector was transformed into the E. coli non-expression host strain, NovaBlue (Novagen, Madison, Wis.) to obtain high plasmid yields. The transformed cells were plated out on LB agar. Ten colonies were selected and grown up in LB broth containing ampicillin (100 μg/mL) at 37° C. The plasmid was purified according to the method described in the Wizard planned purification system (Promega, Madison, Wis.). The gene was sequenced in all ten plasmids to confirm the gene sequence and to check for the absence of PCR errors. The correct construct was then used to transform the tightly regulated E. coli host expression strain (BL21(DE3)pLysS) where expression is under the control of a T7 promotor. The transformed cells were grown at 37° C. to an optical density of 0.4 OD at 600 nm in LB broth and then induced with IPTG (1 mM) for three h. Transformed cells have now been grown in volumes as large as a 10l fermentor. Induction with IPTG produced inclusion bodies that amounted to ~15% of the total cell protein and which were about 75% enriched in D1 protease.

Purification and Enzyme Activity

After induction, the cells were harvested by centrifugation and resuspended in 20 mM HEPES-NaOH buffer, pH 7.3, containing 0.1% TRITON X-100, 0.1 mg/mL lysozyme, 5 mM $MgCl_2$, 0.01 mg/mL RNAse and 0.05 mg/mL DNAse at room temperature. The suspension was spun down and the supernatant discarded. The pellet was resuspended in 20 mM HEPES-NaOH, pH 7.3, 1 mM EDTA, 0.1% TRITON X-100 and 0.3 M NaCl. The suspension was again spun down and the supernatant discarded. The pellet (90% enriched in the thioredoxin-D1 protease fusion) was resuspended in 20 mM HEPES-NaOH, pH 7.3, 1 mM EDTA and 5 mM DTT. All centrifugation steps were for 15 min at 12,000 rpm.

The pellets were solubilized in 8 M guanidinium hydrochloride, 5 mM EDTA in 20 mM HEPES-NaOH, pH 7.3 at 1 mg protein/mL. The protein was refolded by 1:100 dilution into 20 mM MES, pH 6.0, 20 mM CHAPS, 10% glycerol, 1 mM reduced glutathione, 1 mM oxidized glutathione. The concentrated protein was added either dropwise or with a peristaltic pump at a rate of 10 mL in 30–40 min to 1 liter of five additions were made with a one h interval between each addition for a total of 50 mg protein. The solution was then incubated overnight at 4° C. The protein was then concentrated at 4° C. using a YM30 membrane in an Amicon concentration cell. The concentrated protein was then loaded onto a MonoQ (HR10/10, Pharmacia,) column equilibrated with 15 mM CHAPS (3-[(3-cholamidopropyl)-dimethyl-ammonio]-1-propane sulfonate), 10% glycerol and 20 mM HEPES-NaOH, pH 7.3. The protein was eluted using a NaCl gradient from 0–400 mM in the same buffer. The fractions containing purified protease were then concentrated and further purified to homogeneity on a TSK4000 (G4000SW, 21.5×600 mm, TosoHaas) column with 15 mM CHAPS, 10% glycerol and 20 mM HEPES-NaOH, pH 7.3 as elution buffer. Cleavage of the N-terminal tags with enterokinase produces mature D1 protease with only three additional residues at its N-terminus. N-terminal cleavage increases about five-fold the specific activity of the protease.

The enzymatic activity of the recombinant enzyme was assayed by using the microtiter plate ELISA assay with PSII core complexes from Scenedesmus LF-1 as substrate. The specific activity of the recombinant enzyme, expressed in relative units, is close to that of the natural enzyme isolated from wheat leaves.

Example 7

Synthesis of Chloromethyl Ketone Inhibitors as Potential D1 Protease Inhibitors

A variety of chloromethyl ketones were synthesized as potential D1 protease inhibitors.

Abbreviations used in the following discussion of synthesis are listed below.

LRMS: Low Resolution Mass Spectrometry
HRMS: High Resolution Mass Spectrometry
FAB: fast atom bombardment
CI: chemical ionization
Ala: L-alanine
Leu: L-leucine
Asp: L-aspartatic acid
Boc: t-butoxycarbonyl
Bzl: benzyl
Z: benzyloxycarbonyl
DCC: dicyclohexylcarbodiimide
Su: succinimidyl
THF: tetrahydrofuran
DMF: dimethyl formamide Preparation of Boc-Ala-CH$_2$Cl
A. Generation of Diazomethane In a 500 mL round bottom flask, connected with a 500 mL addition funnel, containing potassium hydroxide (12 g) in water (20 mL) was added diethyl ether (40 mL) and diethyleneglycol monoethyl ether (100 mL), then heated to 70° C. (oil bath). Diazald® (43 g) (Aldrich Chemical Co., Milwaukee, Wis.) in 400 mL of diethyl ether was poured into the addition funnel. As the diethyl ether started to distill, the Diazald® solution was added dropwise over a 30 min period. Ethanol (100 mL) was added to the addition funnel until the distillate became colorless.

B. Preparation of Boc-Ala-CH$_2$N$_2$

Boc-Ala-OH (24.6, 130 mmol) was dissolved in THF (45 mL) and cooled to −20° C. The carboxyl group was activated by adding N-methylmorpholine (14.3 mL) and isobutyl chloroformate (17.0 mL) for 5–10 min. The resulting salt was filtered off and washed with 40 mL of cold THF. The freshly generated diazomethane was poured slowly into the filtrate at 0° C. The resulting mixture was warmed to room temperate after the nitrogen evolution finished. After 1 h stirring at room temp, the solvent was removed by rotavap to give Boc-Ala-CH$_2$N$_2$ as bright solid of 28.9 g.

C. Synthesis of Boc-Ala-CH$_2$Cl

To the crude Boc-Ala-CH$_2$N$_2$ (28.9 g) in diethyl ether (200 mL) was added 5.0 N HCl in dioxane (1 equiv., 28.5 mL) dropwise at 0° C. The solution turned colorless upon addition completion. The resulting solution was washed with cold water (200 mL), sat NaCl (aq) (150 mL×2), dried over Na$_2$SO$_4$. After filtration, the filtrate was concentrated to give crude product of 25.6 g. The crude solid was purified by flash silica gel column chromatography (20% hexane in ethyl acetate) and yielded pure Boc-Ala-CH$_2$Cl of 20 g.

LRMS(CI): m/e calculated for M (C$_9$H$_{16}$ClNO$_3$)+H: 222. Found: 222.

Preparation of H-Asp(OtBu)-Leu-OH

Z-Asp(OtBu)-OH (10.23 g) in THF (50 mL) was added N-methylmorpholine (3.30 mL) and isobutyl chloroformate (3.90 mL) at −20° C. After 10 min, the reaction mixture was added to the solution of H-Leu-OBzl (11.81 g in 50 mL HCl$_3$) at −20° C., followed by addition of triethylamine (4.18 mL). The resulting mixture was allowed to warm to room temp. After filtering off the salt, the filtrate was concentrated to an oil. The oil was dissolved in 100 mL of ethyl acetate; washed with 0.2 N HCl, 5% NaHCO$_3$ and sat. NaCl; dried over Na$_2$SO$_4$. After filtration, the solvent was evaporated to give Z-Asp(OtBu)-Leu-OBzl as an oil of 14.81 g.

The Z-Asp(OtBu)-Leu-OBzl (15.6 g) in methanol (50 mL) was added 10% Pd on carbon (0.17 g) and was hydrogenated on a Paar Shaker. After filtering off the catalyst, the filtrate was concentrated to give a foamy solid. The crude product was triturated with diethyl ether to yield 8.03 g of H-Asp(OtBu)-Leu-OH.

LRMS(CI): m/e calculated for M (C$_{14}$H$_{26}$N$_2$O$_5$)+H: 303. Found: 303.

Preparation of Z-Leu-Asp(OtBu)-Leu-OH

Z-Leu-OH (15.92 g) and N-hydroxysuccinimide (6.9 g) were dissolved in dioxane and cooled to 0° C. To the cooled solution, DCC was added and stirred at 0° C. for 0.5 h, then room temp overnight. After filtering off the byproduct urea, the filtrate was concentrated to give crude Z-Leu-OSu as an oil.

The H-Asp(OtBu)-Leu-OH (3.02 g), sodium bicarbonate (1.68 g), and 30 mL of water were mixed to give a mixture of pH 8. Z-Leu-OSu (3.63 g) in dioxane (30 mL) was added to the mixture and was stirred at room temp for 2 h. The reaction mixture was acidified by addition of conc. HCl to pH 1.0, then was extracted with ethyl acetate (30 mL×3). The combined extracts were dried over Na$_2$SO$_4$, filtered, and concentrated. The crude product was dissolved in methanol and chromatographed on a column of Sephadex™ LH20 to yield Z-Leu-Asp(OtBu)-Leu-OH as a foamy solid (4.43 g).

LRMS(CI): m/e calculated for M (C$_{28}$H$_{43}$N$_3$O$_8$)+H: 550. Found: 550.

Preparation of Z-Leu-Asp(OtBu)-Leu-Ala-CH$_2$Cl

Boc-Ala-CH$_2$Cl (2 g) in 5 equiv of HCl in dioxane was stirred at room temp for 1 h. After removal of solvent, the residue was triturated with diethyl ether to give crude H-Ala-CH$_2$Cl (1.41 g). The Z-Leu-Asp(OtBu)-Leu-OH (2.68 g) and N-methylmorpholine (0.54 mL) were dissolved in THF (25 mL), the cooled to −20° C. Isobutyl chloroformate (0.64 mL) was added to generate the mixed anhydride, which was transferred to the H-Ala-CH$_2$Cl (1.41 g in 10 mL of DMF) solution at −20° C. The resulting mixture was allowed to come to room temp and reaction was completed in 3 h. The salt was removed by filtration. The filtrate was concentrated, redissolved in ethyl acetate (100 mL). The solution was washed with 0.2 N HCl, 5% NaHCO$_3$, sat. NaCl; dried over Na$_2$SO$_4$, filtered, and concentrated to yield crude solid of 3.19 g. The crude Z-Leu-Asp(OtBu)-Leu-Ala-CH$_2$Cl was purified by Sephadex LH20 column chromatography.

LRMS(FAB): m/e calculated for M (C$_{32}$H$_{49}$O$_8$N$_4$Cl)+H: 653. Found: 653.

HRMS(FAB): m/e calculated for [M+H]: 653.3317. Found: 653.3283

Preparation of Z-Leu-Asp-Leu-Ala-CH$_2$Cl

The Z-Leu-Asp(OtBu)-Leu-Ala-CH$_2$Cl (0.653 g) in methylene chloride (5 mL) was stirred with trifluoroacetic acid (5 mL) at room temp for 2 h. After removal of the volatile species, the residue was triturated with diethyl ether to yield Z-Leu-Asp-Leu-Ala-CH$_2$Cl as white powder (0.47 g).

LRMS(FAB): m/e calculated for M (C$_{28}$H$_{41}$ClN$_4$O8)+H: 597. Found: 597.

HRMS(FAB): m/e calculated 597.2691 for [M+H]. Found: 597.2678.

Example 8

Microtiter Plate Assay of D1 Protease
Preparation of Primary Antibody

A synthetic peptide (EVMHERNAHNFPLDLA (SEQ ID NO:18)) identical to the final 16 residues of practically all known sequences of polypeptide D1 [Satoh, (1993) in *The Photosynthetic Reaction Center* (Deisenhofer, J. and Norris, J. R., eds.) Vol. I, pp. 289–318, Academic Press, New York], was synthesized (>95% pure) and coupled to keyhole limpet hemocyanin (KLH) by using glutaraldehyde (Multiple Peptide Systems) at a 1:1 ratio of peptide to KLH (w/w). New Zealand rabbits were immunized using the peptide-KLH conjugate suspended in PBS buffer (3.1 mg/mL) and emulsified by mixing with an equal volume of Freund's Adjuvant and injected into 5–6 subcutaneous dorsal sites for a total volume of 0.6 mL. The initial immunization was followed by three booster injections 21 d apart. The antiserum that was used as primary antibody in the assays was obtained from one rabbit 10 d after the second booster injection. The animals were bled from the ear vein, the blood heated at 37° C. for 1 h, chilled to 0° C. for 15 h and centrifuged. Further purification of the supernatant was not attempted. The serum was frozen and stored at −80° C.

Preparation of Microtiter Plates

PSII core complexes were isolated from Scenedesmus wildtype and LF-1 as described by Diner et al., [*J. Biol. Chem.*, 263, 8972–8980 (1988)] and stored at −80° C. Immediately before use, they were diluted to 2 ng Chl/μL using TBS (20 mM Tris-HCl, pH 8.0, 150 mM NaCl). Each plate requires 5 μg Chl or 2.5 mL of diluted LF-1 cores and 0.2 μg Chl or 100 μL of WT cores. Ten plates were typically prepared at the same time.

Glutaraldehyde (25% solution, EM grade, Electron Microscopy Sciences, Fort Washington, Pa.) was freshly opened from sealed ampoules and was diluted to 0.5% with TBS immediately before use (2.4 mL per plate). Twenty-five μL of the diluted glutaraldehyde were pipetted, using a Costar octapipette, into each well of a 96-well microtiter plate (Nunc Immunoplate Maxisorp, Cat. no. 439454). Twenty-five μL of the diluted LF-1 cores were pipetted per well into all but 3 wells of the plate (in column 12) and the plate shaken to mix the glutaraldehyde and the core complexes. Twenty-five μL of the diluted WT cores were pipetted per well into the remaining 3 wells and the plate again well-shaken to mix the glutaraldehyde and the core complexes. The plates were allowed to stand at room temperature for 1–2 h with continuous shaking at room temperature. The wells of column 12 are not incubated with protease and thereby show the maximum (WT wells) and minimum (LF-1 wells) signals attainable with the D1 protease assay.

At the end of the incubation period, the wells were washed to remove unbound cores and blocked to prevent non-specific protein binding. Both were accomplished by giving each well 3 rinses with TTBS (50 mM Tris-HCl, pH 7.4, 150 mM NaCl, 0.2% Tween 20) and then filling each well with TTBS. The plates were then incubated for 1–2 h at room temperature, after which the wells were again rinsed. The remaining TTBS was aspirated and shaken out of the wells. The plates were then sealed in plastic bags containing a moistened paper towel. The plates were then stored in a −20° C. freezer and could be used over a period of months. It has been observed, however, that the background signal observed in blank wells lacking enzyme gradually increased with storage time.

Assay of Enzyme Activity

The samples to be assayed were diluted to 50 μL with 20 mM HEPES-KOH, pH 7.25, 20% glycerol (assay buffer) and placed in individual assay wells. Usually only rows B-G and columns 2–11 were used for assaying enzyme activity because the wells at the periphery of the plate often gave slightly higher signals. The wells containing the control WT and LF-1 cores in column 12 were also left empty. The samples of D1 protease were typically allowed to incubate for 1 h at room temperature after which each well was given 3 quick rinses with TTBS and then allowed to soak for 2 min. The TTBS was aspirated off and then refilled for another 2 min incubation. This was repeated two more times. The plate was then aspirated dry and turned over to tap any remaining buffer onto a paper towel.

Five μL of primary antibody serum, directed against the final 16 residues of mature D1 polypeptide (Multiple Peptide Systems, see below), was diluted with 5 mL of PBS (1.44 g Na$_2$HPO$_4$, 0.24 g KH$_2$PO$_4$, pH 7.2, 8 g NaCl, 0.2 g KCl and 20 g bovine serum albumin per liter), previously filter sterilized through a 0.2 μm membrane. Fifty microliters of diluted secondary antibody solution were added to each well and the covered plates allowed to incubate on a rotary shaker at 37° C. After 30 min, the plate was washed as above with the 3 cycles of soak and aspiration using TTBS.

Ten μL of goat anti-rabbit conjugated to alkaline phosphatase (Sigma Immunochemicals A-7539) were diluted into 5 mL of TBS (3 g Tris-HCl, pH 8.0, 8 g NaCl, 0.2 g KCl and 20 g bovine serum albumin per liter) previously filter sterilized through a 0.2 μm membrane. Fifty microliters of diluted primary antibody solution were added to each well and the covered plates were allowed to incubate on a rotary shaker at 37° C. After 30 min, the plate was washed as above with the 4 cycles of soak and aspiration using TTBS.

The colorimetric substrate consisted of one 5 mg tablet of p-nitrophenyl phosphate (Kirkegaard & Perry Laboratories, 50-80-01) dissolved in 5 mL of 5×diluted DEA Buffer (Kirkegaard & Perry Laboratories, Gaithersburg, Md., 50-80-02). Fifty microliters of this solution were added to each well and the plate incubated at 37° C. in a microtiter plate reader (Molecular Devices, Thermomax) interfaced to a Macintosh SE/30. The time course of the increase in the concentration of p-nitrophenol was typically determined by monitoring the increase in absorption at 405 minus 650 nm for 10 min. Activity is expressed in terms of mOD/min. Alternatively, the plates were incubated at 37° C. for 1 h and measured by the same wavelength difference after quenching the reaction with 50 μL per of 3 M NaOH. The extent of cleavage of the D1 polypeptide in the test well could be determined by comparison with the control LF-1 and WT wells that had not been incubated with enzyme. The ratio of the signals from these wells were usually 1:15–30, respectively, indicating that the primary antibody directed against the mature C-terminus has a much reduced affinity for the preprocessed C-terminus of the D1 polypeptide.

An example of the dependence of the assay on enzyme concentration is shown in FIG. 1 where the intensity of the color reaction is shown to be proportional to enzyme concentration up to approximately 20% of pre-D1 cleaved.

FIG. 1 is a plot of Scenedesmus D1 protease enzyme activity versus enzyme concentration. Purified enzyme was diluted with assay buffer (20 mM HEPES-KOH, pH 7.25, 20% glycerol) at the indicated relative concentrations and incubated in the microtiter plate wells for 1 h at room temperature. The most concentrated enzyme solution used was approximately 13 nM. At 50 μL/well this is equivalent to 650 fmoles enzyme/well. The ordinate is expressed as the percentage of the signal obtained with a concentration of wildtype PSII cores equal to those of LF-1. One hundred percent corresponds to fully processed cores.

Figure 2:
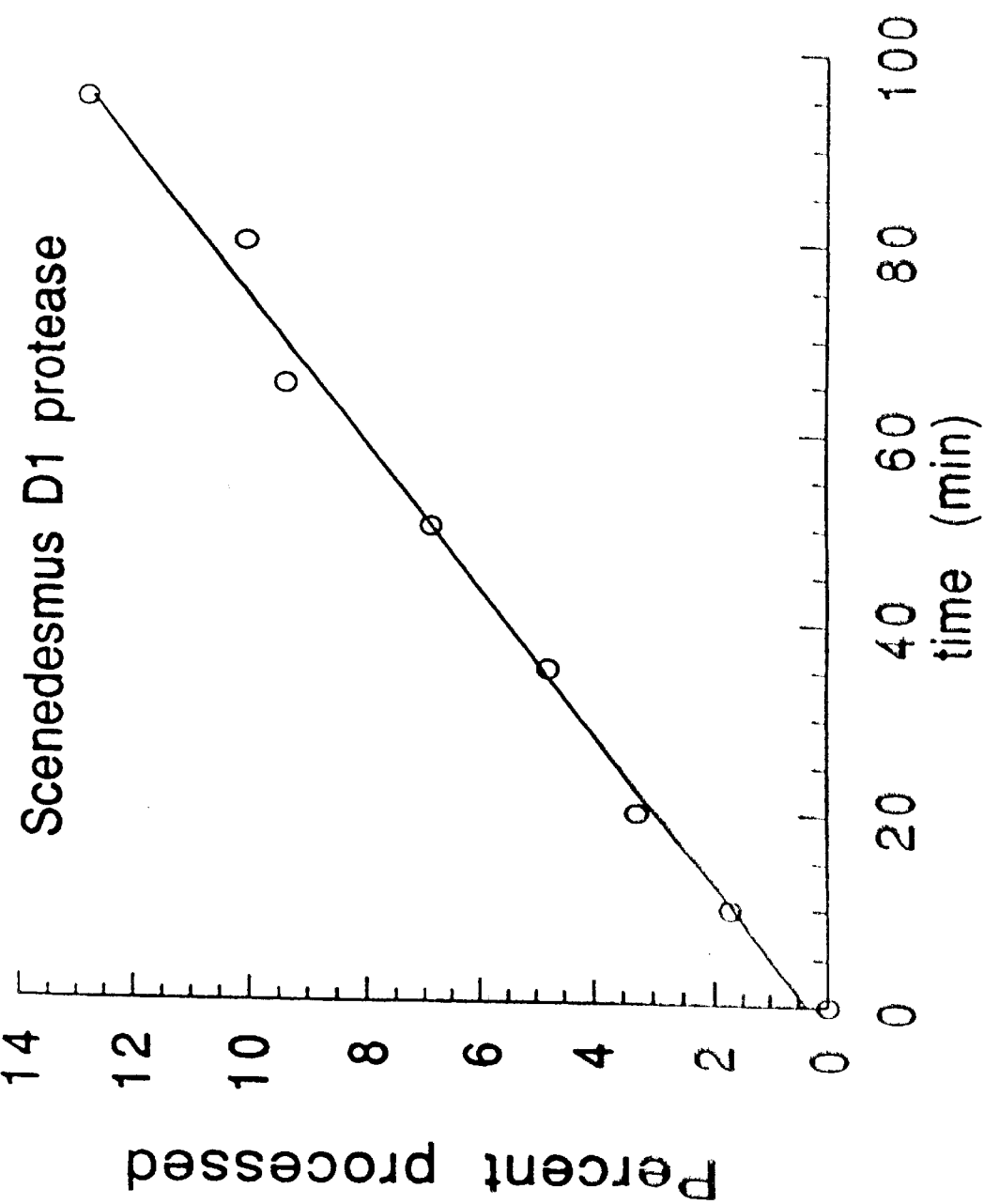
FIG. 2 is a plot of a time course of a D1 protease assay.

As shown in FIG. 2, the assay is also linear with time up to approximately the same percentage of cleaved pre-D1. The optimum pH is 6.3±0.3.

As shown in FIG. 2, purified enzyme was diluted to a concentration of 810 pM or 40 fmoles per well (50 μL) with assay buffer. The enzyme incubated was in the microtiter plate wells at room temperature for the indicated times. The ordinate is expressed as the percentage of the signal obtained with a concentration of wildtype PSII cores equal to those of LF-1. One hundred percent corresponds to fully processed cores.

Example 9

In vitro High-throughput Screening Assay Using Thylakoid Membrane Fragments Containing Pre-D1 and Wheat D1 Protease Example 9 demonstrates an in vitro assay for D1 protease. The assay resulted in the generation of 2 different enzyme products consisting of a mature D1 protein and a C-terminal tail portion of the pre-protein. The assay was capable of detecting both type of products. Because this assay used isolated thylakoid membrane containing the D1 pre-protein substrate the assay could be run at a pH similar to that found in the whole plant.

Detecting the Mature D1 Enzyme Product
Source of Substrate and D1 Protease

The PSII-enriched thylakoid membrane fragment was isolated from Scenedesmus LF-1 mutant cells using a mild TRITON X-100-treatment as follows:

Scenedesmus cells were broken in a "bead-beater" (Biospec Products, Bartlesville, Okla.) in an ice-water bath with 1-mm diameter glass beads using 10 bursts of 45 sec each. The thylakoid membranes were separated from the homogenate using centrifugation, and then the PSII-enriched thylakoid membrane fragment was isolated using TRITON X-100-treatment (TRITON:chlorophyll=15–20:1) and centrifugation according to the procedure described by Miyao et al., [(1991) *Biochim. Biophys. Acta* 1056, 47–56]. The thylakoid membrane fragments contain the unprocessed D1 polypeptide.

Wheat D1-protease was purified from wheat leaves as described in the GENERAL METHODS.
Preparation of Assay Plates The assay made use of a 96-well format multiscreen assay system made by Millipore Corporation (Bedford, Mass., OF1730; cat No. MADV NOB). Each well of the 96-well microtiter plate contained a low-protein-binding Durapore membrane (pore size=0.65 mm). Wells were pre-wet with TBSM (TBS buffer plus 5 mM $MgCl_2$), and then the TBSM solution was removed by drawing the liquid through the membrane using the MultiScreen assay system with its vacuum manifold and pump, according to the manufacturer's instructions. All washes and rinses were performed in a similar manner. Wells were then blocked with the blocking reagent for 5 min as recommended by the manufacturer and the blocking solution was removed by applying vacuum.
Enzyme Assam and Signal Detection A 20–50 μL reaction mixture was added to each well consisting of LF-1 thylakoid membrane, (final PSII reaction center concentration to 0.25 mM) and wheat D1-protease (final enzyme concentration: 200 pM) in reaction buffer (20 mM Mes-NaOH, pH 5.2, 5 mM $MgCl_2$ and 5 mM $MnCl_2$). Plates were incubated for 15 min at room temperature with shaking at which time the reaction liquid was removed and the plate was washed once with TBSM. At this stage, only the thylakoid membrane was left in the well because of the presence of $MgCl_2$. The thylakoid membrane will stack together (as in vivo), and the stacked thylakoid membranes are too large to pass through the plate membrane pore.

Two types of primary antibodies were used. Type 1 was a primary antibody prepared as described in Example 8, containing no reporter. Type 2 affinity purified primary antibody was conjugated to the reporting enzyme Horseradish peroxidase (HRP)(Sigma Chemical Co., St. Louis, Mo.) Both type 1 and type 2 antibodies recognized the mature D1 C-terminus.

Either type 1 or type 2 primary antibody was added into each well, and plates were incubated at 37° C. for 10 min. In assays using type 1 antibody, anti-rabbit IgG alkaline phosphatase conjugate was added to each well and plates were allowed to incubate again at 37° C. for additional 20 min. After this, incubation plates were washed with TBSM to remove the unbound antibodies. When using type 2 antibody for the assay, no secondary antibody was added, and the plate was directly washed after primary antibody incubation.

When using the unlabeled type 1 primary antibody, plus secondary antibody, 50 uL of the colorimetric substrate, p-nitrophenyl phosphate, or fluorescent substrate, Atto-phos (JBL Scientific Inc., San Luispo, Calif.), was added to each well, and plates were incubated for 10–30 min. During the transfer process, the substrate (p-nitrophenyl phosphate or Atto-phos) was separated from the alkaline phosphatase, stopping the reaction automatically.

When using the type 2 HRP conjugated primary antibody 50 mL of colorimetric substrate, TMB (Kirkgaard & Perry Laboratories, Inc., Gaithersburg, Md.) or fluorescent substrate, N-acetyl-3,7-dihydroxyphenoxazine (A6550, Molecular Probes, Inc., Eugene, Oreg.) or chemiluminescence substrate, BM Chemiluminescence ELISA Reagent (Boehringer Mannheim Corp., Indianapolis, Ind.) was added to each well. Plates were incubated for 15 min. Next the substrate was transfered to a regular plastic 96-well microtiter plate using the manifold and vacuum and then read for absorption or fluorescence or chmiluminescence intensity. In the case of fluorescence and chemiluminescence detection, the signal can be directly detected without a filtration step. Measurements can be made in end point or kinetic mode.

Finally, plates were read on a microtiter plate reader, measuring the change in fluorescence or absorption. Control wells included all the same reagents as the experimental with the exception of D1 protease enzyme.

TABLE 4

|  | Without D1P | With D1P |
|---|---|---|
| Type1 AB and PNP (Absorbance OD 450–650) | 0.06 OD | 0.365 OD |
| Type1 AB and ATTOPHOS (Fluorescence intensity) | 414 RU | 1070 RU |
| Type2 AB and TMB (Absorbance at OD 650–450) | 0.023 OD | 0.141 OD |
| Type2 AB and TMB and 7 mM of Z-LDLA-CMK*, ++ (Absorption change) | 0.023 OD | 0.081 OD |
| Type2 AB and A6550 (Fluorescence intensity) | 134 RU | 263 RU |
| Type2 AB and BM (Chemiluminescence intensity) | 16 RU | 33 RU |

*D1 protease has been pre-incubated with Z-LDLA-CMK for 1 h at pH 7.0
++ Z-LDLA-CMK is synthesized as described in Example 7.

Detecting Free C-terminal D1-Tail Enzyme Product
Source of Substrate and D1 Protease As above, LF-1 thylakoid membranes were isolated and used as enzyme substrate. The source of enzyme was recombinant or native purified Wheat D1 -protease.

Molecular Probes

Fluorescamine (Molecular Probe Inc., Eugene, Oreg.) is a molecular probe capable of detecting compounds containing primary amines and were used in this assay method. This probe has the ability to react with N-terminal amines formed on the C-terminal D1-tail portion of the D1 pre-protein, produced as a result of D1 protease action on the substrate.

Assay Method

Assays were run in a 96-well multiscreen plate and prepared as described above.

After incubation with D1 protease the reaction mixture containing the C-terminal D1-tail fragment was transferred to a regular plastic 96-well microtiter plate using a vacuum manifold and pump. The small (approx. size of tail is 1–2 kDa) D1-tail fragment passes through the Durapore® membrane (pore size=0.65 mm) leaving the stacked thyalkoid membranes in the well.

150 mL sodium phosphate buffer (50 mM, pH 8.0) and 50 mL of 1.08 mM fluorescamine in acetone were added to each well and the plate was shaken for 1 min at room temperature. After incubation fluorescence was read on a microtiter plate reader at 400 nm excitation, 460 nm emission.

TABLE 5

| Well with D1 protease | 515 ± 10 relative units |
|---|---|
| Well without D1 protease | 470 ± 10 relative units |

Example 10

In vivo High Throughput Incorporating Scenedesmus Mutant and Wildtype Cells for the Detection of a D1 Protease Inhibitor Example 10 demonstrates an in vivo assay whole cell system to screen for herbicidal agents that target D1 protease. The specific herbicidal agent identified in this example is a known protease inhibitor which comprises a peptide component and will be referred to as IHN-1.

The assay system utilized mutant and wildtype Scenedesmus cells in a reaction mixture that contained a potential D1 protease inhibitor. LF-1 Scenedesmus mutants contain an inactivated D1 protease and are unable to process pre-D1 to the mature protein. Wildtype Scenedesmus contain a functional D1 protease and D1 pre-protein is processed normally. Therefore, in LF-1 cells 100% of D1 protease activity is inhibited. The LF-1 cell shows weaker Fv than that of the wildtype cell [Metz et al., (1980) *Biochem. Biophys. Res. Comm.* 94, 560 566] upon illumination at high light intensity (10–100 photons per sec per center). Furthermore, it has been shown that the Fi of LF-1 cell is 2–3 fold higher than that of the wildtype cell. When Scenedesmus wildtype cells are illuminated in a suitable growth medium containing a D1 protease inhibitor, Fi-increases and an Fv-decreases.

Assay Method

Wildtype and LF-1 mutant cells were suspended in BG-11 liquid growth medium and placed in 96-well plates, and the cell concentration was adjusted to $OD_{730}$=2–3. D1-protease inhibitor was added to each well and both Fo and Fv fluorescence was measured immediately, using a fluorescence microtiter plate reader.

Plates were then placed under strong illumination ($200\mu$ Einsteins·m$^{-2}$·s$^{-1}$) for 1–3 h, and the fluorescence was measured again. The presence of D1 protease inhibitor is confirmed by an Fi-increase and Fv-decrease in the wildtype cells. No change is observed for LF-1 cells (either with or without inhibitor) after the incubation. The wildtype cells without the addition of inhibitor are used as a 0% inhibition control; and the LF-1 cells are used for 100% inhibition control.

Table 6 shows the relative change in Fo and Fv in incubations of mutant and wildtype cells both with and without a D1 protease inhibitor screened in an in vitro assay.

As can be seen by the data in Table 6 there is no Fo and Fv change for (LF-1+IHN-1), even after a 3 h incubation.

TABLE 6

| Time | Fi-(wt) | Fv-(wt) | Fi-(LF1) | Fv-(LF1) | Fi-(wt + INH − 1) | Fv-(wt + INH− 1) |
|---|---|---|---|---|---|---|
| 0 h | 20 | 30 | 45 | 24 | 20 | 30 |
| 3 h | 21 | 32 | 45 | 24 | 25 | 29 |

* Fi measurement: excitation, 360 nm/40 nm band width; emission, 665 nm/20 nm band width; Gain, 80; regular fiber optic bundle
* Fv measurement: excitation, 450 nm/50 nm band width; emission, 665 nm/20 nm band width; Gain, 33; visible fiber optic bundle Example 11

Inhibition Assays Employing an Internally Quenched Fluorescent Peptide as Substrate Example 11 teaches the use of a fluorescence quenching system for the assay of the D1 protease enzyme.

The internally quenched fluorescent substrate was synthesized, purified, and analyzed (mass spectroscopy) by Quality Controlled Biochemicals (Hopkinton, Mass.). The substrate is Ac-NAHN(K-Dnp)PLDLAAVE(K-Mca)PSING-OH [SEQ ID NO:30] where K-Dnp is lysine derivatized in its ε position with 2,4-dintrophenol and K-Mca is lysine derivatized in its ε position with 7-methoxycoumarin-4-acetic acid. The N-terminus is blocked with an acetyl group and the C-terminus is the free acid. Inhibition assays (0.1 ml) included 94 mM MES-NaOH, pH 5.5, 2% DMSO, 10 μM internally quenched substrate, and 1–4 μg wheat D1 protease in the absence and presence of inhibitor. Reactions were initiated with enzyme and allowed to proceed for 1 h at 25° C. when fluorescence intensity of the samples was read using a Cytofluor multiwell plate reader (Millipore, Bedford, Mass.) with excitation and emission wavelengths of 320 nm and 409 nm, respectively. For inhibition assessments, the fluorescence values of samples incubated in the presence of inhibitor were compared to the fluorescence values of samples incubated in the absence of inhibitor.

Fluorescence readings for the control sample containing no enzyme were 1000 fluorescence units, while samples containing active enzyme were measured at 3000 fluorescence units.

What is claimed is:

1. A method for the detection of a D1 protease enzyme activity comprising:
   (i) contacting a derivatized D1 protease substrate with a D1 protease enzyme to form a reaction mixture, the derivatized D1 protease substrate comprising
       (a) a fluorophore; and
       (b) a quenching moiety; and
   (ii) incubating the reaction mixture of step (i) under conditions that permit D1 processing;
   (iii) detecting the processed D1 substrate of step (ii) by a fluorescence detection means.

2. The method of claim 1 wherein the fluorophore is 7-methoxycoumarin-4-acetic acid and the quenching moiety is 2,4-dinitrophenol.

3. The method of claim 2 wherein the fluorophore and the quenching moiety are attached to the derivatized substrate on opposite sides of the D1 processing site.

4. The method of claim 1 wherein the incubating of step (ii) is for about 20 minutes to about 90 minutes and at a temperature range of about 20° C. to about 30° C.

5. The method of claim 4 wherein the temperature is 25° C.

6. The method of claim 1 wherein the derivatized D1 protease substrate is given in Formula I:

Ac-Asn-Ala-His-Asn(Lys-Dnp)Pro-Leu-Asp-Leu-Ala-Ala-Val-Glu(Lys-Mca)Pro-Ser-Ile-Asn-Gly-OH (SEQ ID NO:30)

Wherein:
   Lys-Mca is lysine derivatized in its $\epsilon$ position with 7-methoxycoumarin-4-acetic acid;
   Lys-Dnp is lysine derivatized in its $\epsilon$ position with 2,4-dinitrophenol; and
   Ac is an acetyl group.

7. A derivatized D1 protease substrate as given in Formula I:

Ac-Asn-Ala-His-Asn(Lys-Dnp)Pro-Leu-Asp-Leu-Ala-Ala-Val-Glu(Lys-Mca)Pro-Ser-Ile-Asn-Gly-OH (SEQ ID NO:30)

Wherein:
   Lys-Mca is lysine derivatized in its $\epsilon$ position with 7-methoxycoumarin-4-acetic acid;
   Lys-Dnp is lysine derivatized in its $\epsilon$ position with 2,4-dinitrophenol; and
   Ac is an acetyl group.

* * * * *

SEQUENCE LISTING

<160> NUMBER OF SEQ ID NOS: 30

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:PRIMER A

<400> SEQUENCE: 1
gaaggctggc aggcgtga                                           18

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:PRIMER B

<400> SEQUENCE: 2
ccagtcgcgc atagtaagta tactc                                   25

<210> SEQ ID NO 3
<211> LENGTH: 1680
<212> TYPE: DNA
<213> ORGANISM: SCENEDESMUS

<400> SEQUENCE: 3
ggggtactcc cggacaaact gcttgcaaac cagcgtccga gcaccgcaac cacacttcag     60
gccatttact gcagtcaaaa catgtagaca gcggtgcagc acaactgcag cagcagccaa    120
gcgtgatcag gcgcaagaac agcagccatg gattcaggtt gggctgggcc tgcagctgc    180 tgccactgca gtggcagtgg gcctgggggc agctgcgctg ccggcgcaag cagtgacaag    240
cgagcagctg ctgttcctgg aagcatggcg agcagtggac agggcttatg tggacaaatc    300
gttcaacggg cagagctggt tcaagctacg ggagacgtac cttaagaagg agcccatgga    360
caggcgggcg cagacatatg atgccatccg caagctgctg gcggtgctgg acgacccctt    420
cacgcgcttc ttggagccct cacgcctggc tgcgctgcgg cgaggcacag caggctctgt    480
tacaggtgta ggcttggaga taacgtatga cggcggcagc ggcaaagacg ttgtagtgct    540
gacgcctgcg cctggcgggc cggcagagaa ggctggtgca cgggctggtg atgtcattgt    600
gacagtggat ggcacggctg tgaaggggct gtcgctgtat gacgtgtctg atttgctgca    660
aggagaggct gactcacagg tggaggtggt gctgcatgcg cctggagcac ccagcaacac    720
gcgcacgctg cagctgacgc gccagaaagt gaccatcaac ccagtcacgt tcaccacctg    780
cagcaacgtg gcagcagcag cactgcctcc aggtgccgcg aagcagcagc tgggctatgt    840
gcggctggcc accttcaaca gcaacaccac agcagcagca cagcaggcgt tcacagagct    900
gagcaagcag ggcgtggctg gcttggtgct ggacatacgc aacaacggcg gcggcctgtt    960
cccagcaggt gtgaacgtgg cgcgcatgct ggtggaccgg ggtgatttgg tgctcatcgc   1020

-continued

```
ggacagccag ggcatccgtg acatctactc ggctgacggc aacagcatcg acagtgccac    1080
gccgctggtg gtgctggtca acaggggcac agcctccgcc tcagaggtgc ttgctggcgc    1140
gctgaaggac agcaagcggg gcctcatagc tggcgagcgc acctttggca agggcctcat    1200
tcagactgtg gtggacttgt cggatggctc tggcgtggct gtgacggttg cgcggtacca    1260
gacgccagct ggcgttgaca tcaacaagat aggtgtcagt ccagatgtgc agcttgaccc    1320
agaggtgctg ccgacagatc tggagggggt gtgccgcgtg ctggggtctg atgctgcgcc    1380
gcggctgttt gggtgagctg tcacagcagt gtgtggctgc agggtgtgtt cgtgcgcggg    1440
ggcgcacacg gcactgcaag cgtttgtagg gcaaccggca ctcgagcagc gttgtgacag    1500
cacgcgtcgt tgtcagctcg tgtgagcatc agcaacccg gacaacaagc agcagcagca    1560
ctcgggcgtg cgtgtccctg cacggtcagc tgcacacagt tggcgcgatg gatttgcttg    1620
tcattgcttg ctggctgtcg tggaacgtgg acctgcatac atatcacctt gaaatgatca    1680
```

<210> SEQ ID NO 4
<211> LENGTH: 387
<212> TYPE: PRT
<213> ORGANISM: SCENEDESMUS

<400> SEQUENCE: 4

```
Val Thr Ser Glu Gln Leu Leu Phe Leu Glu Ala Trp Arg Ala Val Asp
  1               5                  10                  15

Arg Ala Tyr Val Asp Lys Ser Phe Asn Gly Gln Ser Trp Phe Lys Leu
             20                  25                  30

Arg Glu Thr Tyr Leu Lys Lys Glu Pro Met Asp Arg Arg Ala Gln Thr
         35                  40                  45

Tyr Asp Ala Ile Arg Lys Leu Leu Ala Val Leu Asp Asp Pro Phe Thr
     50                  55                  60

Arg Phe Leu Glu Pro Ser Arg Leu Ala Ala Leu Arg Arg Gly Thr Ala
 65                  70                  75                  80

Gly Ser Val Thr Gly Val Gly Leu Glu Ile Thr Tyr Asp Gly Gly Ser
                 85                  90                  95

Gly Lys Asp Val Val Val Leu Thr Pro Ala Pro Gly Gly Pro Ala Glu
            100                 105                 110

Lys Ala Gly Ala Arg Ala Gly Asp Val Ile Val Thr Val Asp Gly Thr
        115                 120                 125

Ala Val Lys Gly Leu Ser Leu Tyr Asp Val Ser Asp Leu Leu Gln Gly
    130                 135                 140

Glu Ala Asp Ser Gln Val Glu Val Val Leu His Ala Pro Gly Ala Pro
145                 150                 155                 160

Ser Asn Thr Arg Thr Leu Gln Leu Thr Arg Gln Lys Val Thr Ile Asn
                165                 170                 175

Pro Val Thr Phe Thr Thr Cys Ser Asn Val Ala Ala Ala Leu Pro
            180                 185                 190

Pro Gly Ala Ala Lys Gln Gln Leu Gly Tyr Val Arg Leu Ala Thr Phe
        195                 200                 205

Asn Ser Asn Thr Thr Ala Ala Ala Gln Gln Ala Phe Thr Glu Leu Ser
    210                 215                 220

Lys Gln Gly Val Ala Gly Leu Val Leu Asp Ile Arg Asn Asn Gly Gly
225                 230                 235                 240

Gly Leu Phe Pro Ala Gly Val Asn Val Ala Arg Met Leu Val Asp Arg
                245                 250                 255
```

```
Gly Asp Leu Val Leu Ile Ala Asp Ser Gln Gly Ile Arg Asp Ile Tyr
            260                 265                 270
Ser Ala Asp Gly Asn Ser Ile Asp Ser Ala Thr Pro Leu Val Val Leu
            275                 280                 285
Val Asn Arg Gly Thr Ala Ser Ala Ser Glu Val Leu Ala Gly Ala Leu
            290                 295                 300
Lys Asp Ser Lys Arg Gly Leu Ile Ala Gly Glu Arg Thr Phe Gly Lys
305                 310                 315                 320
Gly Leu Ile Gln Thr Val Val Asp Leu Ser Asp Gly Ser Gly Val Ala
                325                 330                 335
Val Thr Val Ala Arg Tyr Gln Thr Pro Ala Gly Val Asp Ile Asn Lys
            340                 345                 350
Ile Gly Val Ser Pro Asp Val Gln Leu Asp Pro Glu Val Leu Pro Thr
            355                 360                 365
Asp Leu Glu Gly Val Cys Arg Val Leu Gly Ser Asp Ala Ala Pro Arg
            370                 375                 380
Leu Phe Gly
385

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 5
atggactatc ttactgactg c                                              21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 6
gctgaatctt cgaattgccc cttc                                           24

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:PRIMER

<400> SEQUENCE: 7
tctgaacctg gaatctcaca catccttga                                      29

<210> SEQ ID NO 8
<211> LENGTH: 1164
<212> TYPE: DNA
<213> ORGANISM: WHEAT

<400> SEQUENCE: 8
ctcacggagg agaacctgct gttcctggag gcgtggcgcg cggtggaccg cgcctactac    60
gacaagtcct tcaacgggca gagctggttc aggtaccgcg agcgcgccct ccgcgacgac   120
cccatgaaca cgcggcagga gacatatgcg gcgattaaga aaatgcttgc aaccttggat   180
gatccgttca ctcggttatt ggaacccgag aaattcaaga gtttgcggtc tggcacgcaa   240
```

-continued

```
ggtgccctca cgggtgtagg tttatccatc ggctacccgt tggcccttaa aggatcacct    300
gcagggctct ccgtaatgtc agcagcccca ggggtcctg cagaaaaggc gggcattgtg    360
tctggagacg ttattttggc aattgacgac acaagcgcac aagacatgga catatatgac    420
gcagcagatc gcttacaggg tcctgaagga agctcaatag atttgactat ctcagtgga    480 gctgatacca gacatgttgt tttgaagcga gaaagatata cttaaaccc ggtgaggtca    540 aggatgtgtg agattccagg ttcagaggat agctcaaaga ttggttacat caaactaaca    600
acatttaacc aaaatgctgc agggtctgtt aaggaagcca ttaagaaatt aagggagaaa    660
aacgtaaagg cctttgtgtt ggatctgcgg aataacagcg gtggtctttt tcccgaaggg    720
attgagattg cgaagatttg gatggacaag ggtgtcattg tgtatatatg tgatagccgt    780
ggtgtccgtg acatttatga ggcagatgga gctagcacga ttgctgcatc agaaccttta    840
gttgtcctgg taaacaaagg aaccgcaagt gcaagtgaga tccttgcagg agcactgaaa    900
gacaacaaga gggcagtggt gtatggggaa ccaacatatg gaaaaggcaa gatccagtcg    960
gtgtttgcac tgtccgatgg ctcagggttg ccgtgacgg tggcgcgcta cgaaacccct   1020
gcgcatactg acatagataa ggtcggtgtg actccggacc gtccattgcc ggcatcattc   1080
ccgaccgacg aggatggctt ctgcagctgc ctcagggacc cagcttcttg caaccttaat   1140
gctgcccggc tgtttgtgag atcg                                         1164
```

<210> SEQ ID NO 9
<211> LENGTH: 388
<212> TYPE: PRT
<213> ORGANISM: WHEAT

<400> SEQUENCE: 9

```
Leu Thr Glu Glu Asn Leu Leu Phe Leu Glu Ala Trp Arg Ala Val Asp
  1               5                  10                  15

Arg Ala Tyr Tyr Asp Lys Ser Phe Asn Gly Gln Ser Trp Phe Arg Tyr
                 20                  25                  30

Arg Glu Arg Ala Leu Arg Asp Asp Pro Met Asn Thr Arg Gln Glu Thr
             35                  40                  45

Tyr Ala Ala Ile Lys Lys Met Leu Ala Thr Leu Asp Asp Pro Phe Thr
         50                  55                  60

Arg Leu Leu Glu Pro Glu Lys Phe Lys Ser Leu Arg Ser Gly Thr Gln
 65                  70                  75                  80

Gly Ala Leu Thr Gly Val Gly Leu Ser Ile Gly Tyr Pro Leu Ala Leu
                 85                  90                  95

Lys Gly Ser Pro Ala Gly Leu Ser Val Met Ser Ala Pro Gly Gly
            100                 105                 110

Pro Ala Glu Lys Ala Gly Ile Val Ser Gly Asp Val Ile Leu Ala Ile
            115                 120                 125

Asp Asp Thr Ser Ala Gln Asp Met Asp Ile Tyr Asp Ala Ala Asp Arg
130                 135                 140

Leu Gln Gly Pro Glu Gly Ser Ser Ile Asp Leu Thr Ile Leu Ser Gly
145                 150                 155                 160

Ala Asp Thr Arg His Val Val Leu Lys Arg Glu Arg Tyr Thr Leu Asn
                165                 170                 175

Pro Val Arg Ser Arg Met Cys Glu Ile Pro Gly Ser Glu Asp Ser Ser
            180                 185                 190

Lys Ile Gly Tyr Ile Lys Leu Thr Thr Phe Asn Gln Asn Ala Ala Gly
            195                 200                 205
```

```
Ser Val Lys Glu Ala Ile Lys Lys Leu Arg Glu Lys Asn Val Lys Ala
    210                 215                 220
Phe Val Leu Asp Leu Arg Asn Asn Ser Gly Gly Leu Phe Pro Glu Gly
225                 230                 235                 240
Ile Glu Ile Ala Lys Ile Trp Met Asp Lys Gly Val Ile Val Tyr Ile
                245                 250                 255
Cys Asp Ser Arg Gly Val Arg Asp Ile Tyr Glu Ala Asp Gly Ala Ser
            260                 265                 270
Thr Ile Ala Ala Ser Glu Pro Leu Val Val Leu Val Asn Lys Gly Thr
        275                 280                 285
Ala Ser Ala Ser Glu Ile Leu Ala Gly Ala Leu Lys Asp Asn Lys Arg
    290                 295                 300
Ala Val Val Tyr Gly Glu Pro Thr Tyr Gly Lys Gly Lys Ile Gln Ser
305                 310                 315                 320
Val Phe Ala Leu Ser Asp Gly Ser Gly Leu Ala Val Thr Val Ala Arg
                325                 330                 335
Tyr Glu Thr Pro Ala His Thr Asp Ile Asp Lys Val Gly Val Thr Pro
            340                 345                 350
Asp Arg Pro Leu Pro Ala Ser Phe Pro Thr Asp Glu Asp Gly Phe Cys
        355                 360                 365
Ser Cys Leu Arg Asp Pro Ala Ser Cys Asn Leu Asn Ala Ala Arg Leu
    370                 375                 380
Phe Val Arg Ser
385
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 10
ggtcggaagg atctgggtgt c                                          21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:PRIMER

<400> SEQUENCE: 11
atagtaagcc cacacagttt ctc                                        23

<210> SEQ ID NO 12
<211> LENGTH: 1485
<212> TYPE: DNA
<213> ORGANISM: SYNECHOCYSTIS

<400> SEQUENCE: 12
acctagtagt caaggactct aagcaccgcc ccggggttta ttttcttaac taatcttctt    60
caacggtccg gtaaatctca tgttgaagca aaagcgcagt ctaattttgg gaactacagc   120
tctgttattg acaacagtgg cggtgacggg ggttgggttg cgattggccc gctcccaggg   180
ctacctacag gataatctca aggagctggt tgacgaagtt tggcaaattg tcgaccacac   240
ctatgtagat ggtactttca acgtgagga ttgggtagcg gttcgccagg attatctaac   300
acgggactac aaaaaccagg aagaagccta caccgccatt cgggaaatgc tggagaagct   360

-continued

```
aaatgacccc tacactcgct tcatgtcccc cgatgagttt caatcaatgc gtatcgacac    420
ttccggtgaa ttgaccgggg tgggtattca atcacccag gaccaggata cgaagaaaat     480
tgtggtggtg gctcccatcg aagataccccc cgcctacaac gctggcattc tttctaagga   540
cataattacc aagattgacg gtaagtccac cgatggcatg gaagtagatg acgcagtgaa    600
gttaattcgg ggtaagcccg gcaccagtgt ggcgctcact attgagcggg aagggcaggc    660
gatcgaatat cctttgaccc ggactttaat taaaattcat ccagtgcggg cccaagtgga    720
agatattaat ggtgccaggg ttggttatat ccgtttaaat caatccagtg cccaggcttc    780
ggaggaaatg cgccaagcag tgcagaaatt gaaaaagag aatgtggtcg gctacatttt     840
tgacctgcgt tccaatcccg gtggtttgat ctatcccagt gcgaatatcg ctcgcatttg    900
gttggatgaa gggggcattg tgtccaccgt cgatcgccga ggggaagtgg aacaacaaag    960
tgctaacaag cgacagtcga gtaaccgtcc cctagtggcg tcgacgaatg gcggttccgc   1020
cagcgccaat aaaatcatct ccggggcctt acagaataat caacgggccg tcatcgtggg   1080
caccaaaacc tttgataagg aattagtaca atcggtgcgg gagttggggg atggttccgg   1140
tatggcagtg acgatcgcca aatatttaat ccccaacggt cgggacatca ataaacatgg   1200
catcgacccc tatgtggaag tagaactcac cgacgcccag cggaaggaat tgcaacaaaa   1260
tcgggaaaaa gtaggcaccc tggaagaccc ccaatttgcc agggcctatg aagtgctaat   1320
gcaacaggtg aacaaaaccg cttctaagta gcttaagtag gttgaacgag cttgtacaat   1380
ttcattcggt aaaagtctat ggttcaaact gccctacttc ccctcgactt tcccgatcta   1440
tatccggaat ccgacggtaa acccatggct gacaataccc tgcag                   1485
```

<210> SEQ ID NO 13
<211> LENGTH: 391
<212> TYPE: PRT
<213> ORGANISM: SYNECHOCYSTIS

<400> SEQUENCE: 13

```
Gln Gly Tyr Leu Gln Asp Asn Pro Lys Glu Leu Val Asp Glu Val Trp
 1               5                  10                  15

Gln Ile Val Asn Arg Thr Tyr Val Asp Gly Thr Phe Asn Gly Glu Asp
            20                  25                  30

Trp Val Ala Val Arg Gln Asp Tyr Leu Thr Arg Asp Tyr Lys Asn Gln
        35                  40                  45

Glu Glu Ala Tyr Thr Ala Ile Arg Glu Met Leu Glu Lys Leu Asn Asp
    50                  55                  60

Pro Tyr Thr Arg Phe Met Ser Pro Asp Glu Phe Gln Ser Met Arg Ile
65                  70                  75                  80

Asp Thr Ser Gly Glu Leu Thr Gly Val Gly Ile Gln Ile Thr Gln Asp
                85                  90                  95

Gln Asp Thr Lys Lys Ile Val Val Ala Pro Ile Glu Asp Thr Pro
            100                 105                 110

Ala Tyr Asn Ala Gly Ile Leu Ser Lys Asp Ile Ile Thr Lys Ile Asp
        115                 120                 125

Gly Lys Ser Thr Asp Gly Met Glu Val Asp Asp Ala Val Lys Leu Ile
    130                 135                 140

Arg Gly Lys Pro Gly Thr Ser Val Ala Leu Thr Ile Glu Arg Glu Gly
145                 150                 155                 160

Gln Ala Ile Glu Tyr Pro Leu Thr Arg Thr Leu Ile Glu Ile His Pro
                165                 170                 175
```

-continued

Val Arg Ala Gln Val Glu Asp Ile Asn Gly Ala Arg Val Gly Tyr Ile
                180                 185                 190

Arg Leu Asn Gln Phe Ser Ala Gln Ala Ser Glu Glu Met Arg Gln Ala
            195                 200                 205

Val Gln Lys Leu Glu Lys Glu Asn Val Val Gly Tyr Ile Phe Asp Leu
        210                 215                 220

Arg Ser Asn Pro Gly Gly Leu Leu Tyr Ser Ser Val Asp Ile Ala Arg
225                 230                 235                 240

Ile Trp Leu Asp Glu Gly Gly Ile Val Ser Thr Val Asp Arg Arg Gly
                245                 250                 255

Glu Val Glu Gln Gln Ser Ala Asn Lys Arg Gln Leu Ser Asn Arg Pro
            260                 265                 270

Leu Val Val Leu Val Asp Gly Gly Ser Pro Ser Ala Ser Glu Ile Val
        275                 280                 285

Ser Gly Ala Leu Gln Asp Asn Gln Arg Ala Val Ile Val Gly Thr Lys
290                 295                 300

Thr Phe Gly Lys Gly Leu Val Gln Ser Val Arg Glu Leu Gly Asp Gly
305                 310                 315                 320

Ser Gly Met Ala Val Thr Ile Ala Lys Tyr Leu Thr Pro Asn Gly Arg
                325                 330                 335

Asp Ile Asn Lys His Gly Ile Asp Pro Asp Val Glu Val Glu Leu Thr
            340                 345                 350

Asp Ala Gln Arg Lys Glu Leu Gln Gln Asn Arg Glu Lys Val Gly Thr
        355                 360                 365

Leu Glu Asp Pro Gln Phe Ala Arg Ala Tyr Glu Val Leu Met Gln Gln
    370                 375                 380

Val Asn Lys Thr Ala Ser Lys
385                 390

<210> SEQ ID NO 14
<211> LENGTH: 1994
<212> TYPE: DNA
<213> ORGANISM: TOBACCO

<400> SEQUENCE: 14
aggaattcgg cacgagacta gaaaaagggg ataagagaag gaaaaaaaag aaagaagcaa      60
aacgataaca aacagaattg aaaacgaaat tgagcaatgg aagctcttct gggaagctct     120
cattctcctt cagcctctgt atctccttca ttcatcatca ccagtagcta tagaaaaaac     180
cccaccattg cgtttaaggt gctttcgtgg attctttgta cagtggaagt aataactctc     240
gactatatcc tcctatattg tgtcttaaaa agagtggcaa tgacaactct ggaagttgct     300
ctccttcata ctgcattgag caaatgtgca gaaacaaaat gttttctcag ccaaactgga     360
ggcatagcaa actattcatt gataagcaaa gttttctggt tacacaaaat ggcttagctt     420
ttctaccaag aaaattcaga accattctcc gcaaaacagt aaaacattca gaatattta     480 ggaatatagt acctgatata tttgttcggt cctgcattgg actaatgctg ttatggcac     540 ttaatgctgc tgttgcaaaa gctccttctt ttgctctcac tgaacaaaat ctgcttttct     600
tggaggcatg gagaacaatt gaccgtgcat atattgacaa gaccttcaat ggtcaaagtt     660
ggtttaggta cagagaagat gcactacgga aagaaccaat gaacactaga caggaaacgt     720
atgcagcaat aaaaaagatg attgccactc tggatgaccc ttttacccgt tttctggagc     780
ctgaaaagtt taaagtttg cggtccggaa ctcaaaatgc acttactgga gtagggttgt     840

-continued

```
caattggcta tccaacagga aaaactgaat cagctcctgg actggtcgtc gtctcagctt    900
ctccaggagg ttctgcagat agggtctggc atctcatcgg tgatattatc ctagaaattg    960
acaattccag cacagataac atgggtatat atgatgcagc agaacggtta caaggacctg   1020
aaggaagtgg tgtggaacta actgtacgtc gtggatccga dacaaggaac ctaccattga   1080
tacgggagaa agttttgctt aatcctgtaa aatcaagaat ctgcaagctg cccacgggag   1140
gagatgatgc tccacagatt ggatacatca aactatcaac attcaaccaa atgcttctg    1200
gtgctgtaag agaagcgatc gaagccttaa ggaaaaacaa tgttaatgcc tttgtgttgg   1260
accttcggga taatagtggt ggtctcttcc cagaaggagt tgagatacga aaaatttggt   1320
taaacaaggg tgtgattgta tacatttgtg atagccgtgg tgttcgagat atttatgaca   1380
cggatgggag caatgtggta gctgcttcag aaccccctagc agtgctggta aacaaaggga   1440
ctgcaagcgc aagtgagatt ttagcaggtg ctttgaaaga taataagcga gcccagcttt   1500
ttggtgaacc aacatatggc aagggtaaaa tccagtcagt attccagcta tcagatggct   1560
ctggcttggc tgttacagtt gctcggtatg aaactcctgc tcacaacgat atagacaagg   1620
ttggtgtaat tccggaccat cctttgccag cttcattccc aaaagacgac gagagcttct   1680
gtaactgcct tctaaatcct gcctctgctt gccacctaaa cagagtcgag ctattctcga   1740
aataactaca tccctacagt ctgaagaaaa gatcttgttt ttcaacttgt gtttgtagat   1800
tccatagtttt ccatttgatt cttttggcag atgcaagttg gtgattttgc ttgcatgcat   1860
ctgatgtctg tacataccat gaacaaagga caacttcaat ttctattgtt gaactcttgc   1920
tgtaatagaa tcaaattcaa tagtttatca atcatctttt gaactctaaa gcaaaaaaa    1980
aaaaaaaaac tcga                                                    1994
```

<210> SEQ ID NO 15
<211> LENGTH: 473
<212> TYPE: PRT
<213> ORGANISM: TOBACCO

<400> SEQUENCE: 15

```
Met Cys Arg Asn Lys Met Phe Ser Gln Pro Asn Trp Arg His Ser Lys
  1               5                  10                  15

Leu Phe Ile Asp Lys Gln Ser Phe Leu Val Thr Gln Asn Gly Leu Ala
             20                  25                  30

Phe Leu Pro Arg Lys Phe Arg Thr Ile Leu Arg Lys Thr Val Lys His
         35                  40                  45

Ser Glu Ile Phe Arg Asn Ile Val Pro Asp Ile Phe Val Arg Ser Cys
     50                  55                  60

Ile Gly Leu Met Leu Val Met Ala Leu Asn Ala Ala Val Ala Lys Ala
 65                  70                  75                  80

Pro Ser Phe Ala Leu Thr Glu Gln Asn Leu Leu Phe Leu Glu Ala Trp
                 85                  90                  95

Arg Thr Ile Asp Arg Ala Tyr Ile Asp Lys Thr Phe Asn Gly Gln Ser
            100                 105                 110

Trp Phe Arg Tyr Arg Glu Asp Ala Leu Arg Lys Glu Pro Met Asn Thr
        115                 120                 125

Arg Gln Glu Thr Tyr Ala Ala Ile Lys Lys Met Ile Ala Thr Leu Asp
    130                 135                 140

Asp Pro Phe Thr Arg Phe Leu Glu Pro Glu Lys Phe Lys Ser Leu Arg
145                 150                 155                 160

Ser Gly Thr Gln Asn Ala Leu Thr Gly Val Gly Leu Ser Ile Gly Tyr
```

-continued

```
                   165                 170                 175
        Pro Thr Gly Lys Thr Glu Ser Ala Pro Gly Leu Val Val Ser Ala
                        180                 185                 190
        Ser Pro Gly Gly Ser Ala Asp Arg Val Trp His Leu Ile Gly Asp Ile
                    195                 200                 205
        Ile Leu Glu Ile Asp Asn Ser Ser Thr Asp Asn Met Gly Ile Tyr Asp
        210                 215                 220
        Ala Ala Glu Arg Leu Gln Gly Pro Glu Gly Ser Gly Val Glu Leu Thr
        225                 230                 235                 240
        Val Arg Arg Gly Ser Glu Thr Arg Asn Leu Pro Leu Ile Arg Glu Lys
                        245                 250                 255
        Val Leu Leu Asn Pro Val Lys Ser Arg Ile Cys Lys Leu Pro Thr Gly
                    260                 265                 270
        Gly Asp Asp Ala Pro Gln Ile Gly Tyr Ile Lys Leu Ser Thr Phe Asn
                    275                 280                 285
        Gln Asn Ala Ser Gly Ala Val Arg Glu Ala Ile Glu Ala Leu Arg Lys
                290                 295                 300
        Asn Asn Val Asn Ala Phe Val Leu Asp Leu Arg Asp Asn Ser Gly Gly
        305                 310                 315                 320
        Leu Phe Pro Glu Gly Val Glu Ile Arg Lys Ile Trp Leu Asn Lys Gly
                        325                 330                 335
        Val Ile Val Tyr Ile Cys Asp Ser Arg Gly Val Arg Asp Ile Tyr Asp
                    340                 345                 350
        Thr Asp Gly Ser Asn Val Val Ala Ala Ser Glu Pro Leu Ala Val Leu
                    355                 360                 365
        Val Asn Lys Gly Thr Ala Ser Ala Ser Glu Ile Leu Ala Gly Ala Leu
                370                 375                 380
        Lys Asp Asn Lys Arg Ala Gln Leu Phe Gly Glu Pro Thr Tyr Gly Lys
        385                 390                 395                 400
        Gly Lys Ile Gln Ser Val Phe Gln Leu Ser Asp Gly Ser Gly Leu Ala
                        405                 410                 415
        Val Thr Val Ala Arg Tyr Glu Thr Pro Ala His Asn Asp Ile Asp Lys
                    420                 425                 430
        Val Gly Val Ile Pro Asp His Pro Leu Pro Ala Ser Phe Pro Lys Asp
                    435                 440                 445
        Asp Glu Ser Phe Cys Asn Cys Leu Leu Asn Pro Ala Ser Ala Cys His
            450                 455                 460
        Leu Asn Arg Val Glu Leu Phe Ser Lys
        465                 470
```

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:PRIMER

<400> SEQUENCE: 16
cagccatggc gctcacggag gagaac                                            26

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 17
atacttggga tccatatcac g                                          21

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence:PEPTIDE

<400> SEQUENCE: 18

Glu Val Met His Glu Arg Asn Ala His Asn Phe Pro Leu Asp Leu Ala
 1               5                  10                  15

<210> SEQ ID NO 19
<211> LENGTH: 1864
<212> TYPE: DNA
<213> ORGANISM: SPINACH

<400> SEQUENCE: 19

| | | | | | |
|---|---|---|---|---|---|
| gtttcaatgg | aggttatctc | gcgcctcacc | tttgcttccg | tttcttatcc | cttcatttct |   60 |
| tccaacctta | atccaacacc | catgctcaat | tctttcaatt | tcagggtgct | ttcctggaac |  120 |
| agtgccccca | caaatgttgc | agaagctcat | ctccaccgcc | ttttactgag | gaaattgaat |  180 |
| cctgctaatg | atcgggttgt | tgggatctct | aactttggtt | gttcatgccg | gttagatctt |  240 |
| tggccaagtt | ggagacgtca | taagaggtta | tttttccaga | atggtgtatc | tacaataagg |  300 |
| tgggaggtca | agaagtgcag | tcccaaattt | tataagatag | tcagcaacta | tgaaaaatgc |  360 |
| aaacgtcata | tctatgtccc | ctttgttcgt | ttggttgttg | gagttgtatt | gcttatgtct |  420 |
| gtttccgtag | ctttaaacca | gggcccatct | tggtcccttt | ctgaggagaa | tcgaattttc |  480 |
| ctagaagcgt | ggagaacaat | agatcgtgct | tatgttgaca | aaacttttaa | tggacaaagt |  540 |
| tggtttcgct | ataggggagaa | tgcactgcgc | aatgagccga | tgaacagcag | agaagagaca |  600 |
| tataccgcaa | taagaaagat | ggttgctaca | ctgaatgatc | cattcactcg | ttttctggaa |  660 |
| cccgaaaaat | taaagagttt | gcggtctgga | actcagagtt | cgcttacggg | tgtagggata |  720 |
| tctattggcc | ccaccgccgt | tgaccaatca | tccactggat | tagttgtaat | ctcagctact |  780 |
| cctggggctc | ctgccagtag | ggccggcatc | ttgcctggtg | atgtaatatt | ggcaattgat |  840 |
| gatgcaagta | ctgacaaaat | gggcatatat | gaggcagcaa | atatcttaca | gggacctgat |  900 |
| ggaagttctg | ttgatttgac | tatttgcagc | agggatgaga | taaaacatgt | ggtgctgaag |  960 |
| cgtgagagaa | taactctaag | cccagtaaaa | tccagattat | gtgagatgcc | tggttcagca | 1020 |
| aaggatgctc | ctccaaaagt | tggatatatc | aagttaacat | cgttcactga | gaatgcttct | 1080 |
| gatgcagtaa | aggaagctat | agagacactt | agaagtaaca | atgttaatgc | ttttgtgctg | 1140 |
| gaccttcgag | ataatagcgg | tggtctcttt | ccagagggaa | tcgagatagc | caaaatttgg | 1200 |
| ttgaacaaag | gagttattgt | atatatatgt | gatagtcgtg | gtgttcgtga | tatatatgat | 1260 |
| gttgaaggga | gcagtgctgt | agctggttca | gaacctcttg | ttgttctggt | gaacaaggga | 1320 |
| actgcaagtg | ctagtgaaat | attagctggg | gcattaaagg | acaacaaacg | agcagtggta | 1380 |
| tttggagagc | ccacatatgg | aaagggcaag | atacagtcag | ttttcgagct | atctgatgga | 1440 |
| tctggcttag | cagtcacagt | tgctcgctat | gagactcctg | ctcacacaga | tattgacaag | 1500 |
| gtgggaatca | aaccagatca | tcctctccca | gcatctttc | caaaggatga | aaatgatttc | 1560 |
| tgcacctgcg | tccaagatcc | atcgtctact | tgttatctca | acggcgtaca | actcttttca | 1620 |

-continued

```
agatgactat ggaaatgaat ttcttcggtg ttttccattt gcgttgcaaa ttttggttct    1680
tttaaaatta ctattttttc aggatgctag ccatctctgt tgtaagtttg taacatcatt    1740
ggttccttgt atatctcttc atcatcgttc aacatcata gattctttgt atatctcttt     1800
atcgtcgttc gcgaaattca gcatggatta tcttttatca aacaatctaa ctttgagtaa    1860
atct                                                                 1864
```

<210> SEQ ID NO 20
<211> LENGTH: 539
<212> TYPE: PRT
<213> ORGANISM: SPINACH

<400> SEQUENCE: 20

| Met | Glu | Val | Ile | Ser | Arg | Leu | Thr | Phe | Ala | Ser | Val | Ser | Tyr | Pro | Phe |
|---|---|---|---|---|---|---|---|---|---|---|---|---|---|---|---|
| 1 | | | | 5 | | | | | 10 | | | | | 15 | |

| Ile | Ser | Ser | Asn | Leu | Asn | Pro | Thr | Pro | Met | Leu | Asn | Ser | Phe | Asn | Phe |
|---|---|---|---|---|---|---|---|---|---|---|---|---|---|---|---|
| | | | 20 | | | | | 25 | | | | | 30 | | |

| Arg | Val | Leu | Ser | Trp | Asn | Ser | Ala | Pro | Thr | Asn | Val | Ala | Glu | Ala | His |
|---|---|---|---|---|---|---|---|---|---|---|---|---|---|---|---|
| | | | 35 | | | | | 40 | | | | | 45 | | |

| Leu | His | Arg | Leu | Leu | Leu | Arg | Lys | Leu | Asn | Pro | Ala | Asn | Asp | Arg | Val |
|---|---|---|---|---|---|---|---|---|---|---|---|---|---|---|---|
| | 50 | | | | | 55 | | | | | 60 | | | | |

| Val | Gly | Ile | Ser | Asn | Phe | Gly | Cys | Ser | Cys | Arg | Leu | Asp | Leu | Trp | Pro |
|---|---|---|---|---|---|---|---|---|---|---|---|---|---|---|---|
| 65 | | | | | 70 | | | | | 75 | | | | | 80 |

| Ser | Trp | Arg | Arg | His | Lys | Arg | Leu | Phe | Phe | Gln | Asn | Gly | Val | Ser | Thr |
|---|---|---|---|---|---|---|---|---|---|---|---|---|---|---|---|
| | | | | 85 | | | | | 90 | | | | | 95 | |

| Ile | Arg | Trp | Glu | Val | Lys | Lys | Cys | Ser | Pro | Lys | Phe | Tyr | Lys | Ile | Val |
|---|---|---|---|---|---|---|---|---|---|---|---|---|---|---|---|
| | | | 100 | | | | | 105 | | | | | 110 | | |

| Ser | Asn | Tyr | Glu | Lys | Cys | Lys | Arg | His | Ile | Tyr | Val | Pro | Phe | Val | Arg |
|---|---|---|---|---|---|---|---|---|---|---|---|---|---|---|---|
| | | | 115 | | | | | 120 | | | | | 125 | | |

| Leu | Val | Val | Gly | Val | Val | Leu | Leu | Met | Ser | Val | Ser | Val | Ala | Leu | Asn |
|---|---|---|---|---|---|---|---|---|---|---|---|---|---|---|---|
| | 130 | | | | | 135 | | | | | 140 | | | | |

| Gln | Gly | Pro | Ser | Trp | Ser | Leu | Ser | Glu | Glu | Asn | Arg | Ile | Phe | Leu | Glu |
|---|---|---|---|---|---|---|---|---|---|---|---|---|---|---|---|
| 145 | | | | | 150 | | | | | 155 | | | | | 160 |

| Ala | Trp | Arg | Thr | Ile | Asp | Arg | Ala | Tyr | Val | Asp | Lys | Thr | Phe | Asn | Gly |
|---|---|---|---|---|---|---|---|---|---|---|---|---|---|---|---|
| | | | | 165 | | | | | 170 | | | | | 175 | |

| Gln | Ser | Trp | Phe | Arg | Tyr | Arg | Glu | Asn | Ala | Leu | Arg | Asn | Glu | Pro | Met |
|---|---|---|---|---|---|---|---|---|---|---|---|---|---|---|---|
| | | | 180 | | | | | 185 | | | | | 190 | | |

| Asn | Ser | Arg | Glu | Glu | Thr | Tyr | Thr | Ala | Ile | Arg | Lys | Met | Val | Ala | Thr |
|---|---|---|---|---|---|---|---|---|---|---|---|---|---|---|---|
| | | | 195 | | | | | 200 | | | | | 205 | | |

| Leu | Asn | Asp | Pro | Phe | Thr | Arg | Phe | Leu | Glu | Pro | Glu | Lys | Leu | Lys | Ser |
|---|---|---|---|---|---|---|---|---|---|---|---|---|---|---|---|
| | 210 | | | | | 215 | | | | | 220 | | | | |

| Leu | Arg | Ser | Gly | Thr | Gln | Ser | Ser | Leu | Thr | Gly | Val | Gly | Ile | Ser | Ile |
|---|---|---|---|---|---|---|---|---|---|---|---|---|---|---|---|
| 225 | | | | | 230 | | | | | 235 | | | | | 240 |

| Gly | Pro | Thr | Ala | Val | Asp | Gln | Ser | Ser | Thr | Gly | Leu | Val | Val | Ile | Ser |
|---|---|---|---|---|---|---|---|---|---|---|---|---|---|---|---|
| | | | | 245 | | | | | 250 | | | | | 255 | |

| Ala | Thr | Pro | Gly | Ala | Pro | Ala | Ser | Arg | Ala | Gly | Ile | Leu | Pro | Gly | Asp |
|---|---|---|---|---|---|---|---|---|---|---|---|---|---|---|---|
| | | | 260 | | | | | 265 | | | | | 270 | | |

| Val | Ile | Leu | Ala | Ile | Asp | Asp | Ala | Ser | Thr | Asp | Lys | Met | Gly | Ile | Tyr |
|---|---|---|---|---|---|---|---|---|---|---|---|---|---|---|---|
| | | | 275 | | | | | 280 | | | | | 285 | | |

| Glu | Ala | Ala | Asn | Ile | Leu | Gln | Gly | Pro | Asp | Gly | Ser | Ser | Val | Asp | Leu |
|---|---|---|---|---|---|---|---|---|---|---|---|---|---|---|---|
| | 290 | | | | | 295 | | | | | 300 | | | | |

| Thr | Ile | Cys | Ser | Arg | Asp | Glu | Ile | Lys | His | Val | Val | Leu | Lys | Arg | Glu |
|---|---|---|---|---|---|---|---|---|---|---|---|---|---|---|---|
| 305 | | | | | 310 | | | | | 315 | | | | | 320 |

| Arg | Ile | Thr | Leu | Ser | Pro | Val | Lys | Ser | Arg | Leu | Cys | Glu | Met | Pro | Gly |
|---|---|---|---|---|---|---|---|---|---|---|---|---|---|---|---|

```
                    325                 330                 335
        Ser Ala Lys Asp Ala Pro Lys Val Gly Tyr Ile Lys Leu Thr Ser
                    340                 345                 350
        Phe Thr Glu Asn Ala Ser Asp Ala Val Lys Glu Ala Ile Glu Thr Leu
                    355                 360                 365
        Arg Ser Asn Asn Val Asn Ala Phe Val Leu Asp Leu Arg Asp Asn Ser
            370                 375                 380
        Gly Gly Leu Phe Pro Glu Gly Ile Glu Ile Ala Lys Ile Trp Leu Asn
        385                 390                 395                 400
        Lys Gly Val Ile Val Tyr Ile Cys Asp Ser Arg Gly Val Arg Asp Ile
                        405                 410                 415
        Tyr Asp Val Glu Gly Ser Ser Val Ala Gly Ser Glu Pro Leu Val
                    420                 425                 430
        Val Leu Val Asn Lys Gly Thr Ala Ser Ala Ser Glu Ile Leu Ala Gly
                    435                 440                 445
        Ala Leu Lys Asp Asn Lys Arg Ala Val Val Phe Gly Glu Pro Thr Tyr
            450                 455                 460
        Gly Lys Gly Lys Ile Gln Ser Val Phe Glu Leu Ser Asp Gly Ser Gly
        465                 470                 475                 480
        Leu Ala Val Thr Val Ala Arg Tyr Glu Thr Pro Ala His Thr Asp Ile
                        485                 490                 495
        Asp Lys Val Gly Ile Lys Pro Asp His Pro Leu Pro Ala Ser Phe Pro
                    500                 505                 510
        Lys Asp Glu Asn Asp Phe Cys Thr Cys Val Gln Asp Pro Ser Ser Thr
                    515                 520                 525
        Cys Tyr Leu Asn Gly Val Gln Leu Phe Ser Arg
                    530                 535

<210> SEQ ID NO 21
<211> LENGTH: 128
<212> TYPE: PRT
<213> ORGANISM: Scenedesmus

<400> SEQUENCE: 21

Gly Thr Ala Gly Ser Val Thr Gly Val Gly Leu Glu Ile Thr Tyr Asp
        1               5                   10                  15
        Gly Gly Ser Gly Gly Leu Ser Leu Tyr Asp Val Ser Asp Leu Leu Gln
                    20                  25                  30
        Gly Glu Ala Asp Ser Gln Val Glu Val Leu His Ala Pro Gly Ala
                    35                  40                  45
        Pro Ser Asn Thr Arg Leu Ala Thr Phe Asn Ser Asn Thr Thr Ala Ala
            50                  55                  60
        Ala Gln Gln Ala Phe Thr Glu Leu Ser Asp Ile Tyr Ser Ala Asp Gly
        65                  70                  75                  80
        Asn Ser Ile Asp Ser Ala Thr Pro Leu Val Leu Val Asn Arg Leu
                        85                  90                  95
        Ile Gln Thr Val Val Asp Leu Ser Asp Ile Gly Val Ser Pro Asp Val
                    100                 105                 110
        Gln Leu Asp Pro Glu Val Leu Pro Thr Asp Leu Glu Gly Val Cys Arg
                    115                 120                 125

<210> SEQ ID NO 22
<211> LENGTH: 464
<212> TYPE: PRT
<213> ORGANISM: Scenedesmus
```

<400> SEQUENCE: 22

| | | | | | | | | | | | | | | |
|---|---|---|---|---|---|---|---|---|---|---|---|---|---|---|
| Met | His | Ser | Arg | Thr | Asn | Cys | Leu | Gln | Thr | Ser | Val | Arg | Ala | Pro | Gln |
| 1 | | | | 5 | | | | | 10 | | | | | 15 |

Met His Ser Arg Thr Asn Cys Leu Gln Thr Ser Val Arg Ala Pro Gln
1               5                   10                  15

Pro His Phe Arg Pro Phe Thr Ala Val Lys Thr Cys Arg Gln Arg Cys
            20                  25                  30

Ser Thr Thr Ala Ala Ala Ala Lys Arg Asp Gln Ala Gln Glu Gln Gln
        35                  40                  45

Pro Trp Ile Gln Val Gly Leu Gly Leu Ala Ala Ala Thr Ala Val
    50                  55                  60

Ala Val Gly Leu Gly Ala Ala Leu Pro Ala Gln Ala Val Thr Ser
65                  70                  75                  80

Glu Gln Leu Leu Phe Leu Glu Ala Trp Arg Ala Val Asp Arg Ala Tyr
                85                  90                  95

Val Asp Lys Ser Phe Asn Gly Gln Ser Trp Phe Lys Leu Arg Glu Thr
            100                 105                 110

Tyr Leu Lys Arg Glu Pro Met Asp Arg Arg Ala Gln Thr Tyr Asp Ala
            115                 120                 125

Ile Arg Lys Leu Leu Ala Val Leu Asp Asp Pro Phe Thr Arg Phe Leu
    130                 135                 140

Glu Pro Ser Arg Leu Ala Ala Leu Arg Arg Gly Thr Ala Gly Ser Val
145                 150                 155                 160

Thr Gly Val Gly Leu Glu Ile Thr Tyr Asp Gly Gly Ser Gly Arg Asp
            165                 170                 175

Val Val Val Leu Thr Pro Ala Pro Gly Gly Pro Ala Glu Arg Ala Gly
            180                 185                 190

Ala Arg Ala Gly Asp Val Ile Val Thr Val Asp Gly Thr Ala Val Lys
    195                 200                 205

Gly Leu Ser Leu Tyr Asp Val Ser Asp Leu Leu Gln Gly Glu Ala Asp
    210                 215                 220

Ser Gln Val Glu Val Val Leu His Ala Pro Gly Ala Pro Ser Asn Thr
225                 230                 235                 240

Arg Thr Leu Gln Leu Thr Arg Gln Lys Val Thr Ile Asn Pro Val Thr
            245                 250                 255

Phe Thr Thr Cys Ser Asn Val Ala Ala Ala Leu Pro Pro Gly Ala
            260                 265                 270

Ala Arg Gln Gln Leu Gly Tyr Val Arg Leu Ala Thr Phe Asn Ser Asn
    275                 280                 285

Thr Thr Ala Ala Ala Gln Gln Ala Phe Thr Glu Leu Ser Lys Gln Gly
    290                 295                 300

Val Ala Gly Leu Val Leu Asp Ile Arg Asn Asn Gly Gly Leu Phe
305                 310                 315                 320

Pro Ala Gly Val Asn Val Ala Arg Met Leu Val Asp Arg Gly Asp Leu
            325                 330                 335

Val Leu Ile Ala Asp Ser Gln Gly Ile Arg Asp Ile Tyr Ser Ala Asp
            340                 345                 350

Gly Asn Ser Ile Asp Ser Ala Thr Pro Leu Val Val Leu Asn Arg
    355                 360                 365

Gly Thr Ala Ser Ala Ser Glu Val Leu Ala Gly Ala Leu Arg Asp Ser
    370                 375                 380

Lys Arg Gly Leu Ile Ala Gly Glu Arg Thr Phe Gly Lys Gly Leu Ile
385                 390                 395                 400

Gln Thr Val Val Asp Leu Ser Asp Gly Ser Gly Val Ala Val Thr Val
            405                 410                 415

Ala Arg Tyr Gln Thr Pro Ala Gly Val Asp Ile Asn Lys Ile Gly Val
            420                 425                 430

Ser Pro Asp Val Gln Leu Asp Pro Glu Val Leu Pro Thr Asp Leu Glu
        435                 440                 445

Gly Val Cys Arg Val Leu Gly Ser Asp Ala Ala Pro Arg Leu Phe Gly
    450                 455                 460

<210> SEQ ID NO 23
<211> LENGTH: 60
<212> TYPE: DNA
<213> ORGANISM: Scenedesmus
<220> FEATURE:
<223> OTHER INFORMATION: Description of Artificial Sequence:PRIMER

<400> SEQUENCE: 23
ctgaaggaca gcaagcgggg cctcatagct ggcgagcgca cctttggcaa gggcctcatt    60

<210> SEQ ID NO 24
<211> LENGTH: 20
<212> TYPE: PRT
<213> ORGANISM: Scenedesmus
<220> FEATURE:
<223> OTHER INFORMATION: Description of Artificial Sequence:PEPTIDE

<400> SEQUENCE: 24

Leu Lys Asp Ser Lys Arg Gly Leu Ile Ala Gly Glx Arg Thr Phe Gly
 1               5                  10                  15

Lys Gly Leu Ile
            20

<210> SEQ ID NO 25
<211> LENGTH: 59
<212> TYPE: DNA
<213> ORGANISM: Scenedesmus
<220> FEATURE:
<223> OTHER INFORMATION: Description of Artificial Sequence:PRIMER

<400> SEQUENCE: 25
ctcaaggaca gcaagcgggc tcatagctg gcgagcgcac ctttggcaag ggcctcatt     59

<210> SEQ ID NO 26
<211> LENGTH: 8
<212> TYPE: PRT
<213> ORGANISM: Scenedesmus
<220> FEATURE:
<223> OTHER INFORMATION: Description of Artificial Sequence:PEPTIDE

<400> SEQUENCE: 26

Leu Lys Asp Ser Lys Arg Ala Ser
 1               5

<210> SEQ ID NO 27
<211> LENGTH: 60
<212> TYPE: DNA
<213> ORGANISM: Scenedesmus
<220> FEATURE:
<223> OTHER INFORMATION: Description of Artificial Sequence:PRIMER

<400> SEQUENCE: 27
ctcaagcaca gcaagcgggc tcattagct ggcgagcgca cctttggcaa gggcctcatt    60

<210> SEQ ID NO 28
<211> LENGTH: 20
<212> TYPE: PRT

-continued

```
<213> ORGANISM: Scenedesmus
<220> FEATURE:
<223> OTHER INFORMATION: Description of Artificial Sequence:PEPTIDE

<400> SEQUENCE: 28

Leu Lys Asp Ser Lys Arg Ala Ser Leu Ala Gly Glx Arg Thr Phe Gly
 1               5                  10                  15

Lys Gly Leu Ile
            20

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence:PRIMER

<400> SEQUENCE: 29
gcccgatcgc ctcata                                                 16

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence:PEPTIDE
      SUBSTRATE
<220> FEATURE:
<221> NAME/KEY: UNSURE
<222> LOCATION: (4)
<223> OTHER INFORMATION: K-2,4-dintrophenol
<220> FEATURE:
<221> NAME/KEY: UNSURE
<222> LOCATION: (13)
<223> OTHER INFORMATION: K-7-methoxycoumarin-4-acetic acid

<400> SEQUENCE: 30

Ala His Asn Lys Pro Leu Asp Leu Ala Ala Val Glu Lys Pro Ser Ile
 1               5                  10                  15

Asn Gly
```